(12) United States Patent
Tulchinsky et al.

(10) Patent No.: US 6,525,143 B2
(45) Date of Patent: Feb. 25, 2003

(54) DENDRITIC MACROMOLECULES FOR METAL-LIGAND CATALYZED PROCESSES

(75) Inventors: Michael Leo Tulchinsky; David James Miller, both of Charleston, WV (US)

(73) Assignee: Union Carbide Chemicals & Plastics Technology Corporation, Danbury, CT (US)

(*) Notice: Subject to any disclaimer, the term of this patent is extended or adjusted under 35 U.S.C. 154(b) by 0 days.

(21) Appl. No.: 09/991,572

(22) Filed: Nov. 16, 2001

(65) Prior Publication Data

US 2002/0111438 A1 Aug. 15, 2002

Related U.S. Application Data

(62) Division of application No. 09/697,837, filed on Oct. 27, 2000, now Pat. No. 6,350,819.

(51) Int. Cl.[7] ............................ C08F 8/40; C07C 45/00; C08G 79/04

(52) U.S. Cl. .................... 525/330.4; 528/167; 502/162; 568/8; 568/454

(58) Field of Search ...................... 525/330.4; 528/167; 502/162; 568/8, 454

(56) References Cited

U.S. PATENT DOCUMENTS

| | | | |
|---|---|---|---|
| 4,568,737 A | 2/1986 | Tomalia et al. ............. | 528/332 |
| 4,769,498 A | 9/1988 | Billig et al. ................ | 568/454 |
| 4,879,418 A | 11/1989 | Bach et al. ................. | 568/454 |
| 5,059,710 A | 10/1991 | Abatjoglu et al. ............ | 558/78 |
| 5,138,101 A | 8/1992 | Devon ........................ | 568/492 |
| 5,180,854 A | 1/1993 | Abatjoglou et al. ........ | 568/454 |
| 5,235,113 A | 8/1993 | Sato et al. ................... | 568/454 |
| 5,312,996 A | 5/1994 | Packett ....................... | 568/454 |
| 5,360,938 A | 11/1994 | Babin et al. ................ | 568/449 |
| 5,387,617 A | 2/1995 | Hedstrand et al. ........... | 521/79 |
| 5,393,795 A | 2/1995 | Hedstrand et al. .......... | 521/134 |
| 5,393,797 A | 2/1995 | Hedstrand et al. .......... | 521/134 |
| 5,395,979 A | 3/1995 | Deckman et al. ........... | 568/454 |
| 5,463,082 A | 10/1995 | Horvath et al. ............... | 549/46 |
| 5,527,524 A | 6/1996 | Tomalia et al. ............. | 424/133 |
| 5,530,092 A | 6/1996 | Meijer et al. ............... | 528/363 |
| 5,560,929 A | 10/1996 | Hedstrand et al. .......... | 424/486 |
| 5,681,473 A | 10/1997 | Miller et al. ................ | 210/651 |
| 5,714,166 A | 2/1998 | Tomalia et al. ............. | 424/486 |
| 5,773,667 A | 6/1998 | Bahrmann et al. .......... | 568/454 |
| 5,817,884 A | 10/1998 | Bahrmann ................... | 568/454 |
| 5,932,772 A | 8/1999 | Argyropoulos et al. ..... | 568/454 |
| 5,952,530 A | 9/1999 | Argyropoulos et al. ..... | 568/454 |
| 6,225,404 B1 | 5/2001 | Sorensen et al. .......... | 525/54.1 |

FOREIGN PATENT DOCUMENTS

| | | |
|---|---|---|
| DE | 2 326 489 | 12/1974 |
| DE | 4 321 194 A1 | 1/1995 |
| EP | 0097891 | 1/1984 |
| FR | 2 734 268 | 5/1995 |
| WO | 00/02656 | 1/2000 |
| WO | 00/49066 | 8/2000 |
| WO | 01/21625 | 3/2001 |

OTHER PUBLICATIONS

Bardaji, M. et al., "Phosphorus–Containing Dendrimers as Multidentate Ligands: Palladium, Platinum, and Rhodium Complexes," *Organometallics*, vol. 16, 1997, pp. 403–410.

Galliot, C. et al., "Polyaminophosphines Containing Dendrimers. Synthesis and Characterizations," *Journal of Am. Chemical Soc.* vol. 117, 1995, pp. 5470–5476.

Imyanitov, N.S. et al., "Synthesis of High–Molecular Weight Phosphine Ligands for Catalysts of Homogeneous Reactions*," *Neftekhimiya*, vol. 32(3), 1992, pp. 200–207.

Kanpen, J.W.J., et al, "Homogeneous catalysts based on silane dendrimers functionalized with arylnickel(II) complexes," *Nature*, vol. 372, Dec. 15, 1994, pp. 659–663.

Launay, N., et al., "A General Synthetic Strategy for Neutral Phosphorus–Containing Dendrimers," *Angewandte Chemie International Edition in English*, vol. 33 (15/16,581), 1994, pp. 1589–1592.

Lunay, N. et al., "Synthesis and Reactivity of Unusual Phosphorus Dendrimers. A Useful Divergent Growth Approach Up to the Seventh Generation," *Journal of Am. Chemical Soc.*, vol. 117, 1995, pp. 3282–3283.

Lohmer, G., et al, "Synthesis and Catalytic Activity of Dendritic Diphosphane Metal Complexes," *Angewandte Chemie International Edition, English Version*, vol. 36 (13/14), 1997, pp. 1526–1529.

Miedaner, A. et al., "Electrochemical Reduction of CO2 Catalyzed by Small Organophosphine Dendrimers Containing Palladium," *Inorganic Chem.*, 1994 vol. 33, 5482–5490.

Prevote, D. et al., "Phosphate–, Phosphite–, Ylide–, and Phosphonate–Terminated Dendrimers," *Journal of Organic Chemistry*, vol. 62, 1997, 4834–4841.

Slany, M., et al., "Dendrimers Surface Chemistry, Facile Route to Polyphosphines and Their Gold Complexes," *Journal of Am. Chemical Soc.*, vol. 117, 1995, pp. 9764–9765.

Sournies, F. et al, "Spherical Cyclophosphazene Dendrimers to the Fifth Generation**," *Angewandte Chemie Internation Edition in English*, vol 34(5), 1995, p. 578.

Stinson, S.C., "Delving nto Dendrimers," *C&EN Northeast News Bureau*, Sep. 1997.

Reetz, M. T. et al, "Synthesis and Catalytic Activity of Dendritic Diphosphane Metal Complexes," *Agewandte Chemie, International Edition*, vol. 13/14 No. 36, 1997, pp. 1526–1529. XP002125425.

Sakai, T. et al., "Cooling Compositions," Abstract., *Chemical Abstracts Service*, Columbus, Ohio, XP002202683, 1989.

(List continued on next page.)

*Primary Examiner*—James J. Seidleck
*Assistant Examiner*—Olga Asinovsky

(57) ABSTRACT

This invention relates to dendritic macromolecules and their use in metal-dendritic macroligand complex catalyzed processes, e.g., hydroformylation. The use of metal-dendritic macroligand complex catalysts in such processes facilitates the separation of desired product from catalyst, for example, by membrane filtration.

7 Claims, No Drawings

OTHER PUBLICATIONS

Gololobov, Y. G. et al., ".alpha.–Alkenyl Analogs of Phosphorylcholines," Abstract., *Chemical Abstracts Service*, Columbus, Ohio, XP002202684, 1990.

Abdou, W. M. et al., "On the Preparation and Pseudorotation of Certain Monocyclic Pentaoxyphosphoranes," Abstract., *Chemical Abstracts Service*, Columbus, Ohio, XP002202685, 1986.

Grechkin, N. P. et al., "Organophosphorus Derivatives of Some N–substituted Lactams," Abstract., *Chemical Abstracts Service*, Columbus Ohio, XP002202686, 1982.

Watanabe, Y. et al., "Utilization of O–xylylene N,N–diethylphosphoramidite for the Synthesis of Phosphoric Diesters," Abstract., *Chemical Abstracts Service*, Columbus, Ohio, XP002202697, 1992.

DENDRITIC MACROMOLECULES FOR METAL-LIGAND CATALYZED PROCESSES

CROSS-REFERENCE TO PRIOR APPLICATION

This application is a divisional of prior application No. 09/697,837 filed Oct. 27, 2000 now U.S. Pat. No. 6,350,819.

BRIEF SUMMARY OF THE INVENTION

Technical Field

This invention relates to dendritic macromolecules and their use in metal-ligand complex catalyzed processes. More particularly this invention relates to metal-dendritic macroligand complex catalyzed processes in which separation of the desired product from the catalyst is facilitated.

BACKGROUND OF THE INVENTION

A number of industrially important processes such as hydrogenation, carbonylation, and hydroformylation involve homogeneous catalysts containing complexes of transition metals with organic ligands. In particular, hydroformylation of olefins to produce aldehydes occurs in the presence of syngas (carbon monoxide and hydrogen) and transition metal complexes with various organophosphorus ligands.

Many transition metal complexes catalyze the hydroformylation reaction, but cobalt and rhodium are especially important industrially. Rhodium catalysts have gained increasing significance over the cobalt ones in hydroformylation due to possibility of low pressure conditions. Employed ligands include predominantly phosphines and phosphites. Phosphite ligands are often preferable due to enhanced hydroformylation activity and excellent selectivity to the desired product. The selectivity involves high regioselectivity (predominant formation of normal versus branched product) and high stereoselectivity (preferential generation of the desired enantiomer or diastereomer). Phosphite ligands can also be tailored to maintain sufficient catalyst stability for industrial applications.

Separation of products from catalysts involving low molecular weight aldehydes is usually performed by the simple physical processes of vaporization or distillation. Difficulties in the recovery and reuse of hydroformylation catalysts and ligands are a concern in commercial processes. It is also commonly recognized that stripping of higher molecular weight products such as C6–C20 aldehydes and especially thermally sensitive carbonyl compounds such as dialdehydes and monoaldehydes with various functional groups using the same separation methods are often problematic. Indeed, heating the corresponding reaction product mixtures may result in the excessive loss of the organophosphorus ligands or irreversible transformations of the target aldehydes. Overcoming these limitations is particularly important for rhodium-based catalysts and organophosphite ligands due to their high cost. Several alternative product removal techniques have been attempted to streamline separation of rhodium catalysts from high boiling aldehyde products. See, for example, U.S. Pat. Nos. 5,138,101, 4,879,418, 5,180,854, 5,463,082, 5,952,530, 5,932,772, 5,395,979, 5,681,473, and 5,773,667.

Attempts also have been made to facilitate separation of catalysts from products in homogeneous catalysis using polysilane dendrimers functionalized with n nickel-containing catalytically active sites (Knapen et al. *Nature* 1994, 372, 659–663). These catalysts are shown to be active for the Kharasch addition of polyhalogenoalkanes to carbon-carbon double bonds. Removal of their complexes from the solution of products are thought to be achievable by ultrafiltration methods but have not been demonstrated experimentally. This article does not disclose dendritic organophosphorus ligands and rhodium catalysts.

Dendrimeric organophosphorus ligands containing phosphine sites capable of complexing to palladium, platinum, and rhodium are known, e. g. Bardaji et al *Organometallics* 1997, 16, 403–410. Applications of dendritic ligands in hydroformylation is documented for phosphine-coated dendrimers (Reetz et al. *Angew. Chem. Int. Ed. Engl.* 1997, 36, 1526–1529). These dendrimers are functionalized with phosphine groups only.

A more efficient and cost effective method for separating catalyst from product in homogeneous catalyzed processes would be highly desirable in the art.

DISCLOSURE OF THE INVENTION

It has now been discovered that in metal- organophosphorus ligand complex catalyzed processes, the desired product can be effectively separated from the catalyst. By the practice of this invention, it is now possible to separate the desired product from the catalyst without the need to use vaporization separation and the harsh conditions associated therewith. This invention facilitates a highly desirable separation which prevents and/or lessens degradation of the organophosphorus ligand and deactivation of the catalyst as occur under harsh conditions with vaporization separation.

It has been discovered that organophosphorus-containing dendritic macromolecules of this invention may be employed as soluble macroligands with nanoscale dimensions and spherical or near-spherical shape, in transition metal complex catalyzed homogeneous processes, such as hydroformylation processes, to provide active, stable and separable transition metal-dendritic macroligand complex catalysts. For example, the organophosphorus-containing dendritic macroligands of this invention are useful in providing unique separation capabilities of products from catalysts while retaining desirable catalytic activity, selectivity and stability. The organophosphorus-containing dendritic macroligands of this invention are especially useful in the processes involving higher molecular weight olefins or thermally sensitive oxo products when separations by vaporization or other known means are limited or impossible.

This invention relates in part to dendritic macromolecules having a core and one or more branches emanating from the core wherein at least a portion of the branches contain terminal groups derived from organophosphites, organophosphonites and/or organophosphinites.

This invention also relates in part to dendritic macromolecules having a core and one or more branches emanating from the core wherein at least a portion of the branches contain terminal groups derived from a trivalent phosphorus-containing group of the formula

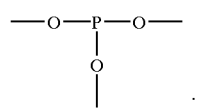

This invention further relates in part to dendritic macromolecules represented by the formula:

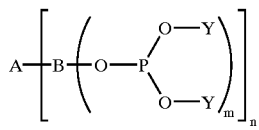

wherein A represents a q-valent dendritic macromolecule radical, each B is the same or different and represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, n is a value of from 1 to about 1000, q equals n, and r equals m+1.

This invention yet further relates in part to a metal-dendritic macroligand complex catalyst comprising a Group 8, 9 or 10 metal complexed with a dendritic macroligand represented by the formula:

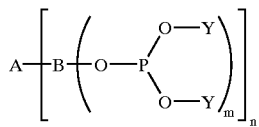

wherein A represents a q-valent dendritic macromolecule radical, each B is the same or different and represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, n is a value of from 1 to about 1000, q equals n, and r equals m+1.

This invention also relates in part to a process for producing one or more products comprising reacting one or more reactants in the presence of a metal-dendritic macroligand complex catalyst to produce said one or more products, in which said metal-dendritic macroligand complex catalyst comprises a Group 8, 9 or 10 metal complexed with a dendritic macroligand represented by the formula:

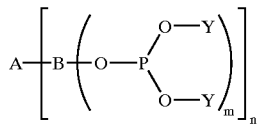

wherein A represents a q-valent dendritic macromolecule radical, each B is the same or different and represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, n is a value of from 1 to about 1000, q equals n, and r equals m+1.

This invention further relates in part to a process for producing one or more products comprising (i) reacting one or more reactants in the presence of a metal-dendritic macroligand complex catalyst to produce said one or more products, and (ii) separating said metal-dendritic macroligand complex catalyst from said one or more products, wherein said metal-dendritic macroligand complex catalyst comprises a Group 8, 9 or 10 metal complexed with a dendritic macroligand represented by the formula:

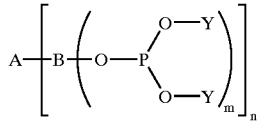

wherein A represents a q-valent dendritic macromolecule radical, each B is the same or different and represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, n is a value of from 1 to about 1000, q equals n, and r equals m+1.

This invention yet further relates in part to a process for the preparation of a dendritic macromolecule which comprises (a) reacting a substituted or unsubstituted organophosphite, organophosphonite or organophosphinite, or a derivative of a substituted or unsubstituted organophosphite, organophosphonite or organophosphinite, with one or more organic or inorganic compounds, wherein said one or more organic or inorganic compounds contain at least two functional groups, to give a functional organophosphite, organophosphonite or organophosphinite, and (b) reacting said functional organophosphite, organophosphonite or organophosphinite with a dendrimer to give said dendritic macromolecule.

This invention also relates in part to a process for the preparation of a dendritic macromolecule which comprises (a) reacting a dendrimer with one or more organic or inorganic compounds, wherein said one or more organic or inorganic compounds contain at least two functional groups, to give a functional dendrimer, and (b) reacting said functional dendrimer with a substituted or unsubstituted organophosphite, organophosphonite or organophosphinite, or a derivative of a substituted or unsubstituted organophosphite, organophosphonite or organophosphinite, to give said dendritic macromolecule.

DETAILED DESCRIPTION

General Processes

The processes of this invention may be asymmetric or non-asymmetric, the preferred processes being non-asymmetric, and may be conducted in any batch, continuous or semi-continuous fashion. The product/catalyst separation is an important feature of this invention and may be conducted as described herein. The processing techniques used in this invention may correspond to any of the known processing techniques heretofore employed in conventional processes. Likewise, the manner or order of addition of the reaction ingredients and catalyst are also not critical and may be accomplished in any conventional fashion. As used herein, the term "reaction product fluid" is contemplated to include, but not limited to, a reaction mixture containing an amount of any one or more of the following: (a) a metal-dendritic macroligand complex catalyst, (b) product(s) formed in the reaction, (c) unreacted reactant(s), and (d) solvent(s).

This invention encompasses the carrying out of known conventional syntheses and product/catalyst separations in a conventional fashion utilizing the dendritic macroligands of this invention. By the practice of this invention, it is possible to separate the desired product from the metal-dendritic macroligand complex catalyst without the need to use vaporization separation and the harsh conditions associated therewith.

Illustrative processes include, for example, hydroformylation, hydroacylation (intramolecular and intermolecular), hydrocyanation, hydroamidation, hydroesterification, amination, alcoholysis, hydrocarbonylation, hydroxycarbonylation, carbonylation, olefin isomerization, transfer hydrogenation and the like. Preferred processes involve the reaction of organic compounds with carbon monoxide, or with carbon monoxide and a third reactant, e.g., hydrogen, or with hydrogen cyanide, in the presence of a catalytic amount of a metal-dendritic macroligand complex catalyst. The most preferred processes include hydroformylation, hydrocyanation, hydrocarbonylation, hydroxycarbonylation and carbonylation.

Hydroformylation can be carried out in accordance with conventional procedures known in the art. For example, aldehydes can be prepared by reacting an olefinic compound, carbon monoxide and hydrogen under hydroformylation conditions in the presence of a metal-dendritic macroligand complex catalyst described herein. Alternatively, hydroxyaldehydes can be prepared by reacting an epoxide, carbon monoxide and hydrogen under hydroformylation conditions in the presence of a metal-dendritic macroligand complex catalyst described herein. The hydroxyaldehyde can be hydrogenated to a diol, e.g., hydroxypropionaldehyde can be hydrogenated to propanediol. Hydroformylation processes are described more fully hereinbelow.

Intramolecular hydroacylation can be carried out in accordance with conventional procedures known in the art. For example, aldehydes containing an olefinic group 3 to 7 carbons removed can be converted to cyclic ketones under hydroacylation conditions in the presence of a metal-dendritic macroligand complex catalyst described herein.

Intermolecular hydroacylation can be carried out in accordance with conventional procedures known in the art. For example, ketones can be prepared by reacting an olefin and an aldehyde under hydroacylation conditions in the presence of a metal-dendritic macroligand complex catalyst described herein.

Hydrocyanation can be carried out in accordance with conventional procedures known in the art. For example, nitrile compounds can be prepared by reacting an olefinic compound and hydrogen cyanide under hydrocyanation conditions in the presence of a metal-dendritic macroligand complex catalyst described herein.

Hydroamidation can be carried out in accordance with conventional procedures known in the art. For example, amides can be prepared by reacting an olefin, carbon monoxide and a primary or secondary amine or ammonia under hydroamidation conditions in the presence of a metal-dendritic macroligand complex catalyst described herein.

Hydroesterification can be carried out in accordance with conventional procedures known in the art. For example, esters can be prepared by reacting an olefin, carbon monoxide and an alcohol under hydroesterification conditions in the presence of a metal-dendritic macroligand complex catalyst described herein.

Amination (or hydro-amino-addition) can be carried out in accordance with conventional procedures known in the art. For example, amines can be prepared by reacting an olefin with a primary or secondary amine under amination conditions in the presence of a metal-dendritic macroligand complex catalyst described herein.

Alcoholysis (or hydro-alkoxy-addition) can be carried out in accordance with conventional procedures known in the art. For example, ethers can be prepared by reacting an olefin with an alcohol under alcoholysis conditions in the presence of a metal-dendritic macroligand complex catalyst described herein.

Hydrocarbonylation can be carried out in accordance with conventional procedures known in the art. For example, alcohols can be prepared by reacting an olefinic compound, carbon monoxide, hydrogen and a promoter under hydrocarbonylation conditions in the presence of a metal-dendritic macroligand complex catalyst described herein.

Hydroxycarbonylation can be carried out in accordance with conventional procedures known in the art. For example, acids can be prepared by reacting an olefinic compound, carbon monoxide, water and a promoter under hydroxycarbonylation conditions in the presence of a metal-dendritic macroligand complex catalyst described herein.

Carbonylation can be carried out in accordance with conventional procedures known in the art. For example, lactones can be prepared by treatment of allylic alcohols with carbon monoxide under carbonylation conditions in the presence of a metal-dendritic macroligand complex catalyst described herein.

Isomerization can be carried out in accordance with conventional procedures known in the art. For example, allylic alcohols can be isomerized under isomerization conditions to produce aldehydes in the presence of a metal-dendritic macroligand complex catalyst described herein.

Transfer hydrogenation can be carried out in accordance with conventional procedures known in the art. For example, alcohols can be prepared by reacting a ketone and an alcohol under transfer hydrogenation conditions in the presence of a metal-dendritic macroligand complex catalyst described herein.

The permissible starting material reactants encompassed by the processes of this invention are, of course, chosen depending on the particular process desired. Such starting materials are well known in the art and can be used in conventional amounts in accordance with conventional methods. Illustrative starting material reactants include, for example, substituted and unsubstituted aldehydes (intramolecular hydroacylation), olefins (hydroformylation, carbonylation, intermolecular hydroacylation, hydrocyanation, hydroamidation, hydroesterification, amination, alcoholysis), ketones (transfer hydrogenation), epoxides (hydroformylation, hydrocyanation), alcohols (carbonylation) and the like. Illustrative of suitable reactants for effecting the processes of this invention are set out in Kirk-Othmer, Encyclopedia of Chemical Technology, Fourth Edition, 1996, the pertinent portions of which are incorporated herein by reference.

Illustrative metal-dendritic macroligand complex catalysts employable in the processes encompassed by this invention as well as methods for their preparation are described herein. In general such catalysts may be preformed or formed in situ and consist essentially of metal in complex combination with a dendritic macroligand. The active species may also contain carbon monoxide and/or hydrogen directly bonded to the metal.

The catalyst useful in the processes includes a metal-dendritic macroligand complex catalyst which can be optically active or non-optically active. The permissible metals which make up the metal-organophosphite ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group 11 metals selected from copper (Cu), silver (Ag), gold (Au) and mixtures thereof, and also Group 6 metals selected from chromium (Cr), molybdenum (Mo), tungsten (W) and mixtures thereof. Mixtures of metals from Groups 6, 8, 9, 10 and 11 may also be used in this invention. The permissible dendritic macromolecules which make up the metal-dendritic macroligand complexes contain terminal groups derived from organophosphites, organophosphonites and/or organophosphinites. Mixtures of such dendritic ligands may be employed if desired in the metal-dendritic macroligand complex catalyst. This invention is not intended to be limited in any manner by the permissible dendritic macroligands or mixtures thereof. It is to be noted that the successful practice of this invention may not depend and may not be predicated on the exact structure of the metal-dendritic macroligand complex species, which may be present in their mononuclear, dinuclear and/or higher nuclearity forms. The metal-dendritic macroligand complex catalysts typically contain many metals so they are preferably polynuclear or multinuclear. Indeed, the exact structure is not known. Although it is not intended herein to be bound to any theory or mechanistic discourse, it appears that the catalytic species may in its simplest form consist essentially of the metal in complex combination with the dendritic macroligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the dendritic macroligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_6H_5CN$, $CH_3CN$, NO, $NH_3$, pyridine, $(C_2H_5)_3N$, monoolefins, diolefins and triolefins, tetrahydrofuran, and the like. It is of course to be understood that the complex species are preferably free of any additional organic ligand or anion that might poison the catalyst or have an undue adverse effect on catalyst performance. It is preferred in the metal-dendritic macroligand complex catalyzed processes, e.g., hydroformylation, that the active catalysts be free of halogen and sulfur directly bonded to the metal, although such may not be absolutely necessary. Preferred metal-dendritic macroligand complex catalysts include rhodium-organophosphite-containing dendritic macroligand complex catalysts.

The number of available coordination sites on such metals is well known in the art. Thus the catalytic species may comprise a complex catalyst mixture, in their monomeric, dimeric or higher nuclearity forms, which are preferably characterized by at least one organophosphite-containing dendritic macromolecule complexed per one atom of metal, e.g., rhodium. For instance, it is considered that the catalytic species of the preferred catalyst employed in a hydroformylation reaction may be complexed with carbon monoxide and hydrogen in addition to the dendritic macroligands in view of the carbon monoxide and hydrogen gas employed by the hydroformylation reaction. In contrast to macroligands derived from regular polymers that contain many inaccessible catalytic sites located throughout the framework of the polymer, the dendritic macroligands of this invention form a catalyst with easily accessible catalytically active sites on the periphery of their molecules.

The dendritic macromolecules that may serve as the ligand of the metal-dendritic macroligand complex catalyst of the processes of this invention may be of the achiral (optically inactive) or chiral (optically active) type and are well known in the art. Achiral dendritic macroligands are preferred.

The dendritic macroligands of this invention include dendritic macromolecules represented by the formula:

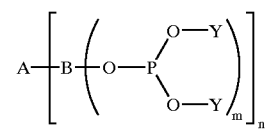

wherein A represents a q-valent dendritic macromolecule radical, each B is the same or different and represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, n is a value of from 1 to about 1000, q equals n, and r equals m+1.

More particularly, the dendritic macroligands of this invention include dendritic macromolecules represented by the formula:

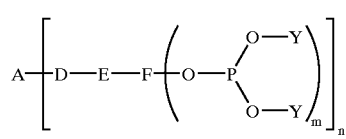

wherein A represents a q-valent dendritic macromolecule radical, each D is the same or different and represents a substituted or unsubstituted divalent organic or inorganic radical, each E is the same or different and represents a substituted or unsubstituted divalent organic or inorganic radical, each F is the same or different and represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, n is a value of from 1 to about 1000, q equals n, and equals m+1.

Illustrative dendritic macroligands of this invention include those of the formulae:

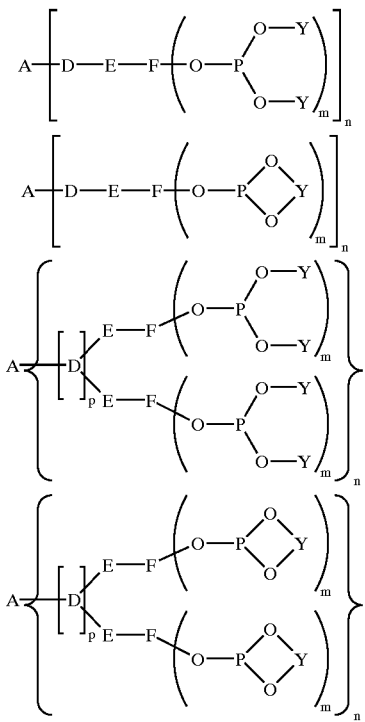

wherein A, D, E, F, Y, m, n, and p are as defined hereinabove.

Among the organophosphites that may serve as terminal groups of the dendritic macromolecules of this invention are monoorganophosphite, diorganophosphite, triorganophosphite and organopolyphosphite compounds. Such organophosphite compounds employable in this invention and/or methods for their preparation are well known in the art.

Illustrative preferred end phosphite groups employable in this invention include those derived from the following structures. Representative monoorganophosphites may include those having the formula:

 (I)

wherein $R^1$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306, the disclosure of which is incorporated herein by reference thereto.

Representative diorganophosphites may include those having the formula:

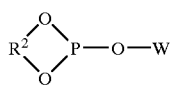 (II)

wherein $R^2$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^2$ include divalent acyclic radicals and divalent aromatic radicals. Illustrative divalent acyclic radicals include, for example, alkylene, alkylene-oxy-alkylene, alkylene-$NR^4$-alkylene wherein $R^4$ is hydrogen or a substituted or unsubstituted monovalent hydrocarbon radical, e.g., an alkyl radical having 1 to 4 carbon atoms; alkylene-S-alkylene, and cycloalkylene radicals, and the like. The more preferred divalent acyclic radicals are the divalent alkylene radicals such as disclosed more fully, for example, in U.S. Pat. Nos. 3,415,906 and 4,567,302 and the like, the disclosures of which are incorporated herein by reference. Illustrative divalent aromatic radicals include, for example, arylene, bisarylene, arylene-alkylene, arylene-alkylene-arylene, arylene-oxy-arylene, arylene-$NR^4$-arylene wherein $R^4$ is as defined above, arylene-S-arylene, and arylene-S-alkylene, and the like. More preferably $R^2$ is a divalent aromatic radical such as disclosed more fully, for example, in U.S. Pat. Nos. 4,599,206, 4,717,775, 4,835,299, and the like, the disclosures of which are incorporated herein by reference.

Representative of a more preferred class of diorganophosphites are those of the formula:

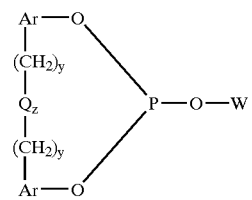 (III)

wherein W is as defined above, each Ar is the same or different and represents a substituted or unsubstituted aryl radical, each y is the same or different and is a value of 0 or 1, Q represents a divalent bridging group selected from —$C(R^3)_2$—, —O—, —S—, —$NR^4$—, $Si(R^5)_2$—and —CO—, wherein each $R^3$ is the same or different and represents hydrogen, an alkyl radical having from 1 to 12 carbon atoms, phenyl, tolyl, and anisyl, $R^4$ is as defined above, each $R^5$ is the same or different and represents hydrogen or a methyl radical, and z is a value of 0 or 1. Such diorganophosphites are described in greater detail, for example, in U.S. Pat. Nos. 4,599,206, 4,717,775, and 4,835,299 the disclosures of which are incorporated herein by reference.

Representative triorganophosphites may include those having the formula:

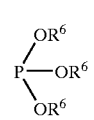 (IV)

wherein each $R^6$ is the same or different and is a substituted or unsubstituted monovalent hydrocarbon radical e.g., an alkyl, cycloalkyl, aryl, alkaryl and aralkyl radicals which may contain from 1 to 24 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6,di-t-butyl-2-naphhyl) phosphite, bis(3,6,8-tri-t-butyl-2-naphthyl)(4-biphenyl) phosphite, bis(3,6,8-tri-t-butyl-2-naphthyl)phenylphosphite, bis(3,6,8-tri-t-butyl-2-naphthyl)(4-benzoylphenyl) phosphite, bis(3,6,8-tri-t-butyl-2-naphthyl)(4-sulfonylphenyl)phosphite, and the like. The most preferred triorganophosphite is triphenylphosphite. Such triorganophosphites are described in greater detail, for example, in U.S. Pat. Nos. 3,527,809 and 5,277,532, the disclosures of which are incorporated herein by reference.

Representative organopolyphosphites contain two or more tertiary (trivalent) phosphorus atoms and may include those having the formula:

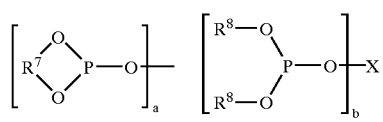
(V)

wherein X represents a substituted or unsubstituted g-valent organic bridging radical containing from 2 to 40 carbon atoms, each $R^7$ is the same or different and represents a divalent organic radical containing from 4 to 40 carbon atoms, each $R^8$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and g equals a+b. Of course it is to be understood that when a has a value of 2 or more, each $R^7$ radical may be the same or different. Each $R^8$ radical may also be the same or different any given compound.

Representative g-valent (preferably divalent) organic bridging radicals represented by X and representative divalent organic radicals represented by $R^7$ above, include both acyclic radicals and aromatic radicals, such as alkylene, alkylene-$Q_z$-alkylene, cycloalkylene, arylene, bisarylene, arylene-alkylene, and arylene-$(CH_2)_y$—$Q_z$—$(CH_2)_y$-arylene radicals, and the like, wherein each Q, y and z are as defined above in Formula (III). The more preferred acyclic radicals represented by X and $R^7$ above are divalent alkylene radicals, while the more preferred aromatic radicals represented by X and $R^7$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative preferred monovalent hydrocarbon radicals represented by each $R^8$ radical above include alkyl and aromatic radicals.

Illustrative preferred organopolyphosphites may include bisphosphites such as those of Formulas (VI) to (VIII) below:

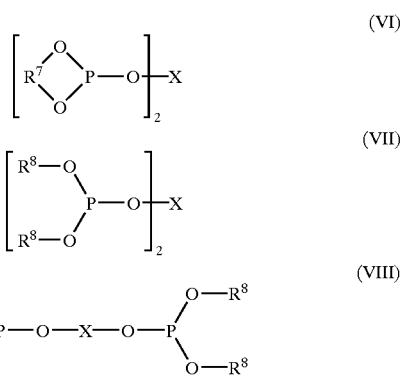

wherein each $R^7$, $R^8$ and X of Formulas (VI) to (VIII) are the same as defined above for Formula (V). Preferably each $R^7$ and X represents a divalent hydrocarbon radical selected from alkylene, arylene, arylene-alkylene-arylene, and bisarylene, while each $R^8$ radical represents a monovalent hydrocarbon radical selected from alkyl and aryl radicals. Organophosphite ligands of such Formulas (V) to (VIII) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following Formulas (IX) to (XI):

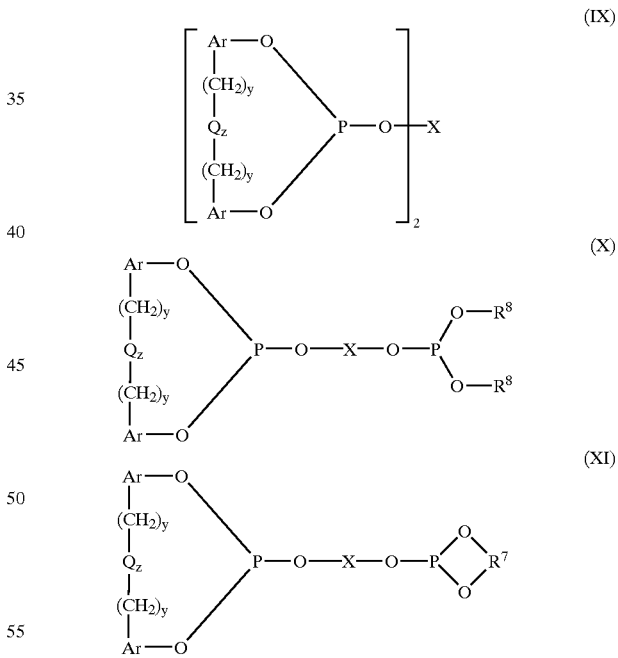

wherein Ar, Q, $R^7$, $R^8$, X, y, and z are as defined above. Most preferably X represents a divalent aryl-$(CH_2)_y$-$(Q)_z$-$(CH_2)_y$-aryl radical wherein each y individually has a value of 0 or 1; z has a value of 0 or 1 and Q is —O—, —S—or —$C(R^3)_2$ where each $R^3$ is the same or different and represents hydrogen or a methyl radical. More preferably each alkyl radical of the above defined $R^8$ groups may contain from 1 to 24 carbon atoms and each aryl radical of the above-defined Ar, X, $R^7$ and $R^8$ groups of the above Formulas (IX) to (XI) may contain from 6 to 18 carbon atoms and said radicals may be the same or different, while the preferred alkylene radicals of X may contain from 2 to 18 carbon atoms and the preferred alkylene radicals of $R^7$ may contain from 5 to 18 carbon atoms. In addition, preferably the divalent Ar radicals and divalent aryl radicals of X of the above formulas are phenylene radicals in which the bridging group represented by —$(CH_2)_y$—$(Q)_z$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organopolyphosphite in the above Formulas (I) to (XI) may be an ionic phosphite, i.e., may contain one or more ionic moieties selected from the group consisting of:

—$SO_3M$ wherein M represents inorganic or organic cation,

—$PO_3M$ wherein M represents inorganic or organic cation,

—$N(R^9)_3X^1$ wherein each $R^9$ is the same or different and represents a hydrocarbon radical containing from 1 to 30 carbon atoms, e.g., alkyl, aryl, alkaryl, aralkyl, and cycloalkyl radicals, and $X^1$ represents inorganic or organic anion, —$CO_2M$ wherein M represents inorganic or organic cation, as described, for example, in U.S. Pat. Nos. 5,059,710; 5,113,022 5,114,473; 5,449,653; and European Patent Application Publication No. 435,084, the disclosures of which are incorporated herein by reference. Thus, if desired, such organopolyphosphite ligands may contain from 1 to 3 such ionic moieties, while it is preferred that only one such ionic moiety be substituted on any given aryl moiety in the organopolyphosphite ligand when the ligand contains more than one such ionic moiety. As suitable counter-ions, M, for the anionic moieties of the ionic organopolyphosphites there can be mentioned hydrogen (i.e. a proton), the cations of the alkali and alkaline earth metals,. e.g., lithium, sodium, potassium, cesium, rubidium, calcium, barium, magnesium and strontium, the ammonium cation and quaternary ammonium cations, phosphonium cations, arsonium cations and iminium cations. Suitable anions, $X^1$, include, for example, sulfate, carbonate, phosphate, chloride, acetate, oxalate and the like.

Of course any of the $R^1$, $R^2$, $R^6$, $R^7$, $R^8$, $R^9$, W, X, Q and Ar radicals of such non-ionic and ionic organophosphites of Formulas (I) to (XI) above may be substituted if desired, with any suitable substituent containing from 1 to 30 carbon atoms that does not unduly adversely affect the desired result of the process of this invention. Substituents that may be on said radicals in addition of course to corresponding hydrocarbon radicals such as alkyl, aryl, aralkyl, alkaryl and cyclohexyl substituents, may include for example silyl radicals such as —$Si(R^{10})_3$; amino radicals such as —$N(R^{10})_2$; phosphine radicals such as —aryl—$P(R^{10})_2$; acyl radicals such as —$C(O)R^{10}$ acyloxy radicals such as —$OC(O)R^{10}$; amido radicals such as —$CON(R^{10})_2$ and —$N(R^{10})COR^{10}$; sulfonyl radicals such as —$SO_2R^{10}$, alkoxy radicals such as —$OR^{10}$; sulfinyl radicals such as —$SOR^{10}$, sulfenyl radicals such as —$SR^{10}$, phosphonyl radicals such as —$P(O)(R^{10})_2$, as well as halogen, nitro, cyano, trifluoromethyl, hydroxy radicals, and the like, wherein each $R^{10}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —$N(R^{10})_2$ each $R^{10}$ taken together can also represent a divalent bridging group that forms a heterocyclic radical with the nitrogen atom, and in amido substituents such as —$C(O)N(R^{10})_2$ and —$N(R^{10})COR^{10}$ each $R^{10}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —$OCH_2CH_2OCH_3$, —$O(CH_2CH_2)_2OCH_3$, —$O(CH_2CH_2)_3OCH_3$, and the like; aryloxy radicals such as phenoxy and the like; as well as silyl radicals such as —$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; arylphosphine radicals such as —$P(C_6H_5)_2$, and the like; acyl radicals such as —$C(O)CH_3$, —$C(O)C_2H_5$, —$C(O)C_6H_5$, and the like; carbonyloxy radicals such as —$C(O)OCH_3$ and the like; oxycarbonyl radicals such as —$O(CO)C_6H_5$, and the like; amido radicals such as —$CONH_2$, —$CON(CH_3)_2$, —$NHC(O)CH_3$, and the like; sulfonyl radicals such as —$S(O)_2C_2H_5$ and the like; sulfinyl radicals such as —$S(O)CH_3$ and the like; sulfenyl radicals such as —$SCH_3$, —$SC_2H_5$, —$SC_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H5)$, and the like.

A dendritic macromolecule, also known as a dendrimer, is a three-dimensional, highly ordered oligomeric or polymeric molecule having a well defined chemical structure. The core part of the dendritic macromolecules of this invention consists of a dendrimer as described, for example, in U.S. Pat. Nos. 4,507,466, 4,568,737, 4,631,337, 5,530,092, 5,387,617, 5,393,795, 5,393,797, 5,527,524, 5,560,929 and 5,714,166, WO 0049066, G. R. Newkome et al., *Dendritic Macromolecules. Concepts, Synthesis, Perspectives*, VCH:Weinheim, 1996, and also in Angew, Chem. Int. Ed. Engl. 29:138–175 (1990), the disclosures of which are incorporated herein by reference. One, two or three hydrogens or other monovalent radicals of the terminal functional groups of the conventional dendrimers can be substituted by organophosphite end groups as described herein to give the dendritic macromolecules of this invention. Examples of such conventional dendrimer terminal groups include, for example, amino, amido, hydroxyl, silane, aldehyde, ketone, carboxylic acid, esters and the like. Commercial dendrimers may preferably be used such as Starburst® (PAMAM) dendrimers and DAB-Am polypropyleneimine dendrimers, both commercially available from Aldrich. Dendrimers useful as starting materials in the processes of this invention can be prepared by conventional processes and some are commercially available.

The shape of the core largely determines the three-dimensional shape of the dendritic macromolecules of this invention. For example, if a small molecule is used as the core, a dendritic macromolecule with a spherical shape can be obtained. If a polymer is used as a core, the dendritic macromolecule obtained will tend to have a more longitudinal shape. The theoretical total number of branches emanating from the core of the dendritic macromolecules can be determined by methods known in the art such as, for example, described in U.S. Pat. No. 5,530,092, supra. Typically, the dendritic macromolecule contains from about 1 to about 10 generations of branches, preferably from about 2 to about 10 and more preferably from about 3 to about 9. A preferred dendritic macromolecule can be characterized as having a spherical shape with a polyvalent core that is covalently bonded to at least two ordered dendritic branches which extend through at least two generations. It is understood that the structure of the dendritic macromolecules of this invention may be imperfect, e.g., some dendritic branches may be missing and/or the macromolecule may contain additional branches. The molecular weight of such dendritic macromolecules may be higher or lower than those having a highly ordered structure.

In accordance with an embodiment of this invention, a process for the preparation of a dendritic macromolecule comprises (a) reacting a substituted or unsubstituted organophosphite, organophosphonite or organophosphinite, or a derivative of a substituted or unsubstituted organophosphite, organophosphonite or organophosphinite, (e.g., phosphorochloridite), with one or more organic or inorganic compounds, wherein said one or more organic or inorganic compounds contain at least two functional groups, to give a functional organophosphite, organophosphonite or organophosphinite, and (b) reacting said functional organophosphite, organophosphonite or organophosphinite with a dendrimer to give said dendritic macromolecule.

Illustrative functional organophosphites employable in this invention include those of the formulae:

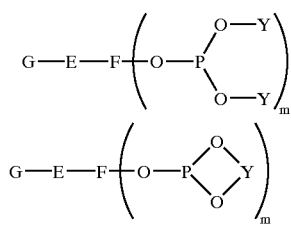

wherein E, F, Y and m are as defined hereinabove, and G is a functional organic or inorganic group which is capable of reacting with the end group of the dendrimer. Illustrative of the suitable G groups are α,β-unsaturated compounds substituted with electron-withdrawing groups including unsaturated aliphatic esters and amides such as, for example, methyl acrylate, ethyl acrylate, butyl acrylate, methacrylic ester, crotylic ester, acrylamide; epoxides such as for instance, ethylene oxide and propylene oxide; acid halides such as, for example, acid chlorides, acryloil chloride, benzoic acid chloride, acetic acid chloride; alkyl halides such as, for instance, epichlorohydrine, ethyl bromoacetate, propyl bromide and allyl bromide; aryl halides such as, for instance, benzyl chloride; tosyl halides such as, for instance, tosyl chloride; anhydrydes, such as, for example, maleic anhydride, succinic anhydride and phthalic anhydride; dicarboxylic acids such as, for instance, terephthalic acid and adipic acid; diols such as, for example, 1,3-propanediol; aldehydes such as, for instance, acetaldehyde, hexanal, benzaldehyde, pyridine aldehydes; ketones such as, for example, cyclohexanones; isocyanate and isothiacyanate.

The functional organophosphite contains three important elements: a coupling group (indicated by G in the above formulae), a spacer (indicated by E in the above formulae) and a catalyst binding site (indicated by the phosphite group in the above formulae). The coupling group reacts with the dendrimer end group and provides the attachment (grafting) of the terminal organophosphite site to the dendrimer. In a preferred embodiment of this invention, the coupling group is an acrylic ester.

The spacer stretches out from the coupling group to the catalyst binding site and functions to reduce sterical congestion when the system runs out of space to accommodate additional catalytic sites. Spacers of the same or different length can be attached to the terminal group of the dendrimer which may allow for effective introduction of organophosphite sites onto the dendrimer. The spacer can consist of at least two atoms, preferably three, more preferably four and greater.

The catalytic properties of the dendritic macroligands are attributable in part to the catalyst binding sites (ligand). Organophosphites are preferable binding sites over phosphines due to higher reaction rates and increased potential to control regioselectivity and stereoselectivity.

An illustrative type of functional organophosphite employable in this invention is represented by the formula:

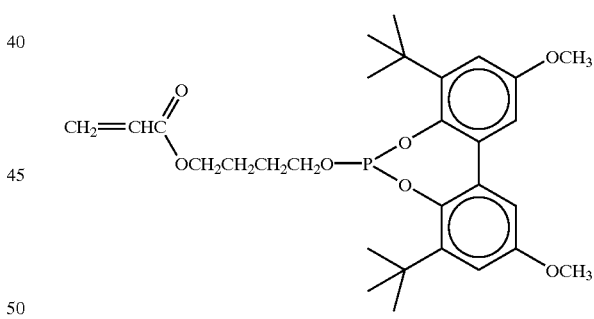

In accordance with another embodiment of this invention, a process for the preparation of a dendritic macromolecule comprises (a) reacting a dendrimer with one or more organic or inorganic compounds, wherein said one or more organic or inorganic compounds contain at least two functional groups, to give a functional dendrimer, and (b) reacting said functional dendrimer with a substituted or unsubstituted organophosphite, organophosphonite or organophosphinite, or a derivative of a substituted or unsubstituted organophosphite, organophosphonite or organophosphinite, (e.g., phosphorochloridite), to give said dendritic macromolecule.

Illustrative preferred dendritic macromolecules of this invention include those represented by the formulae:

17 18
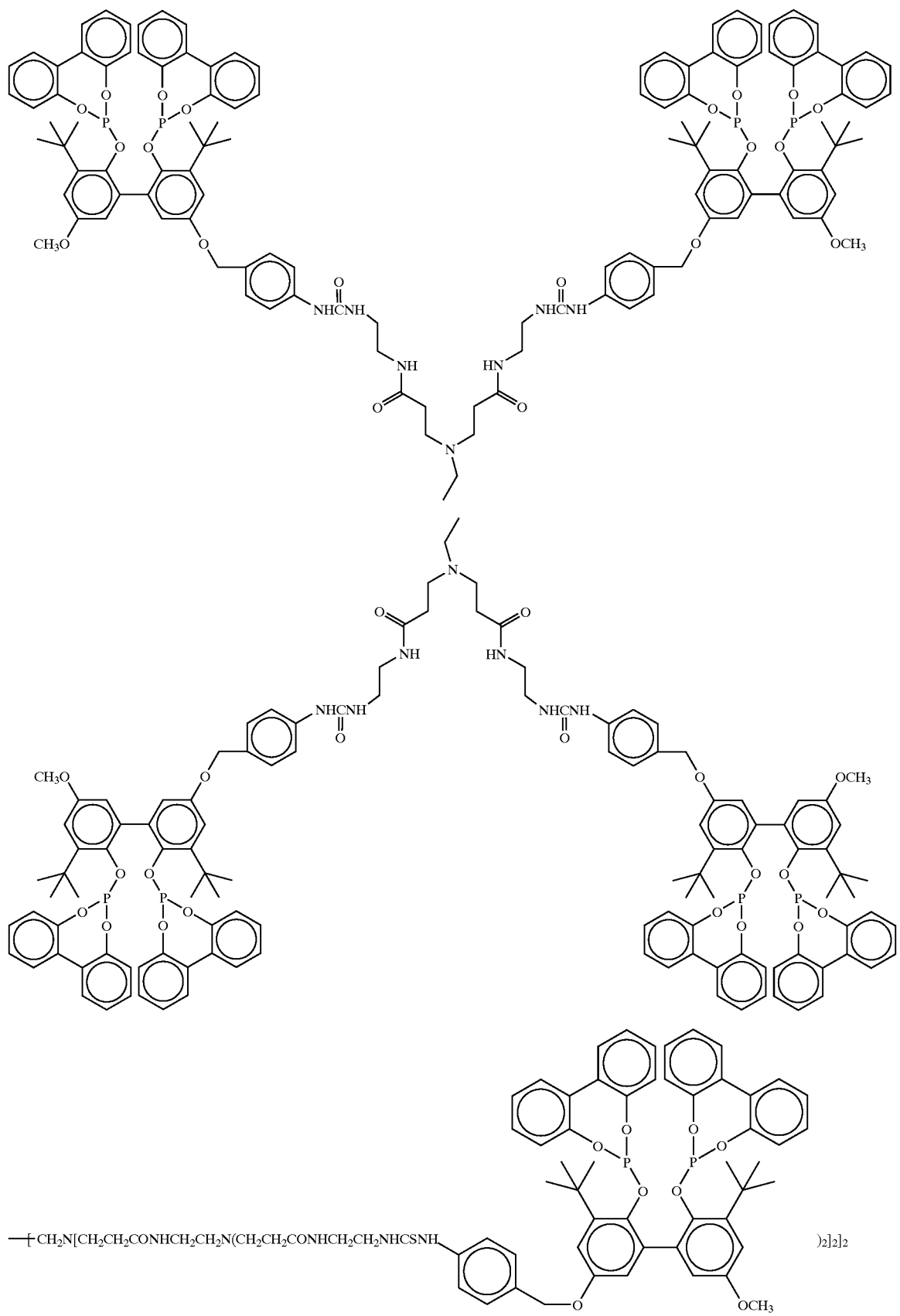

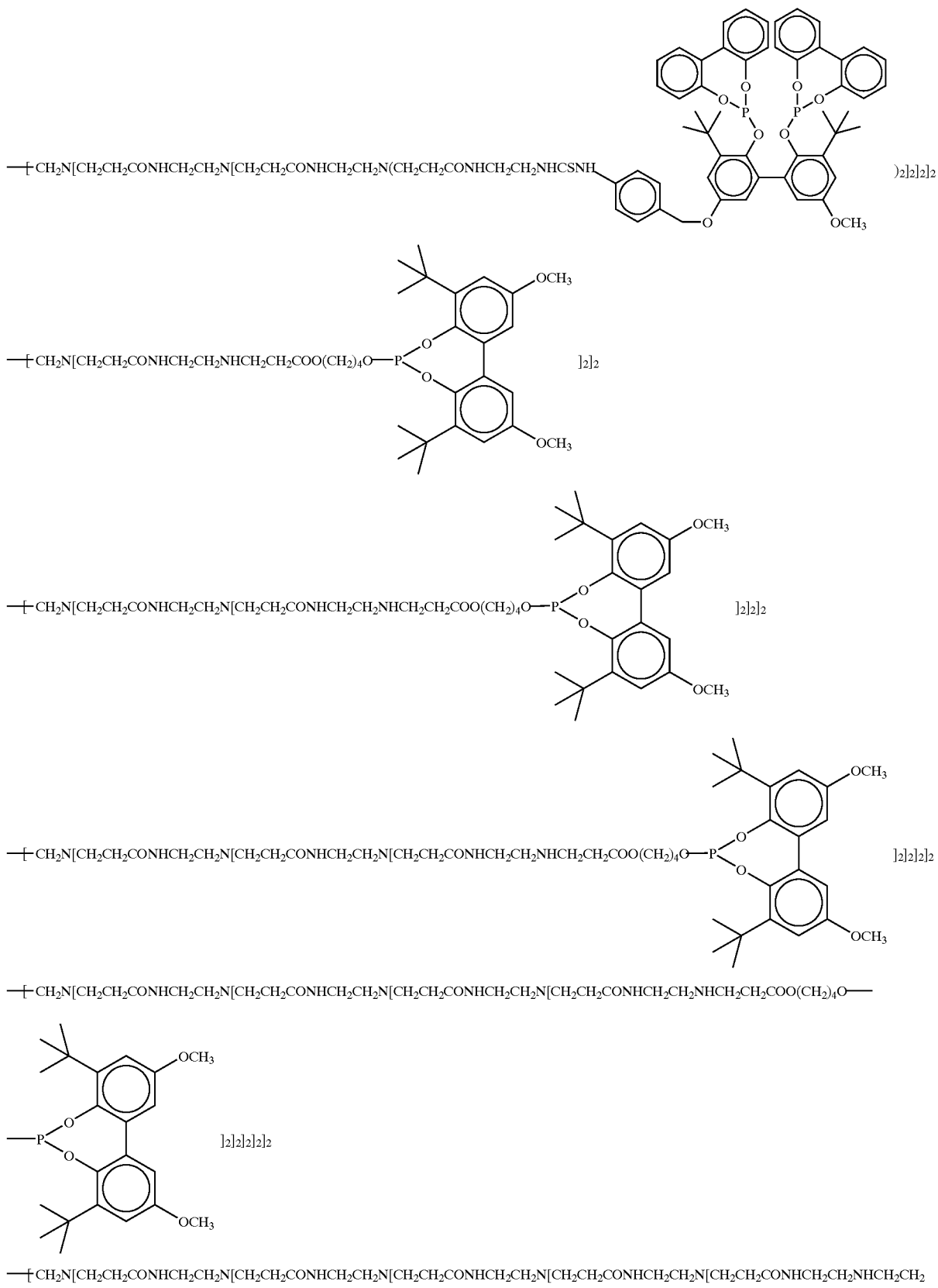

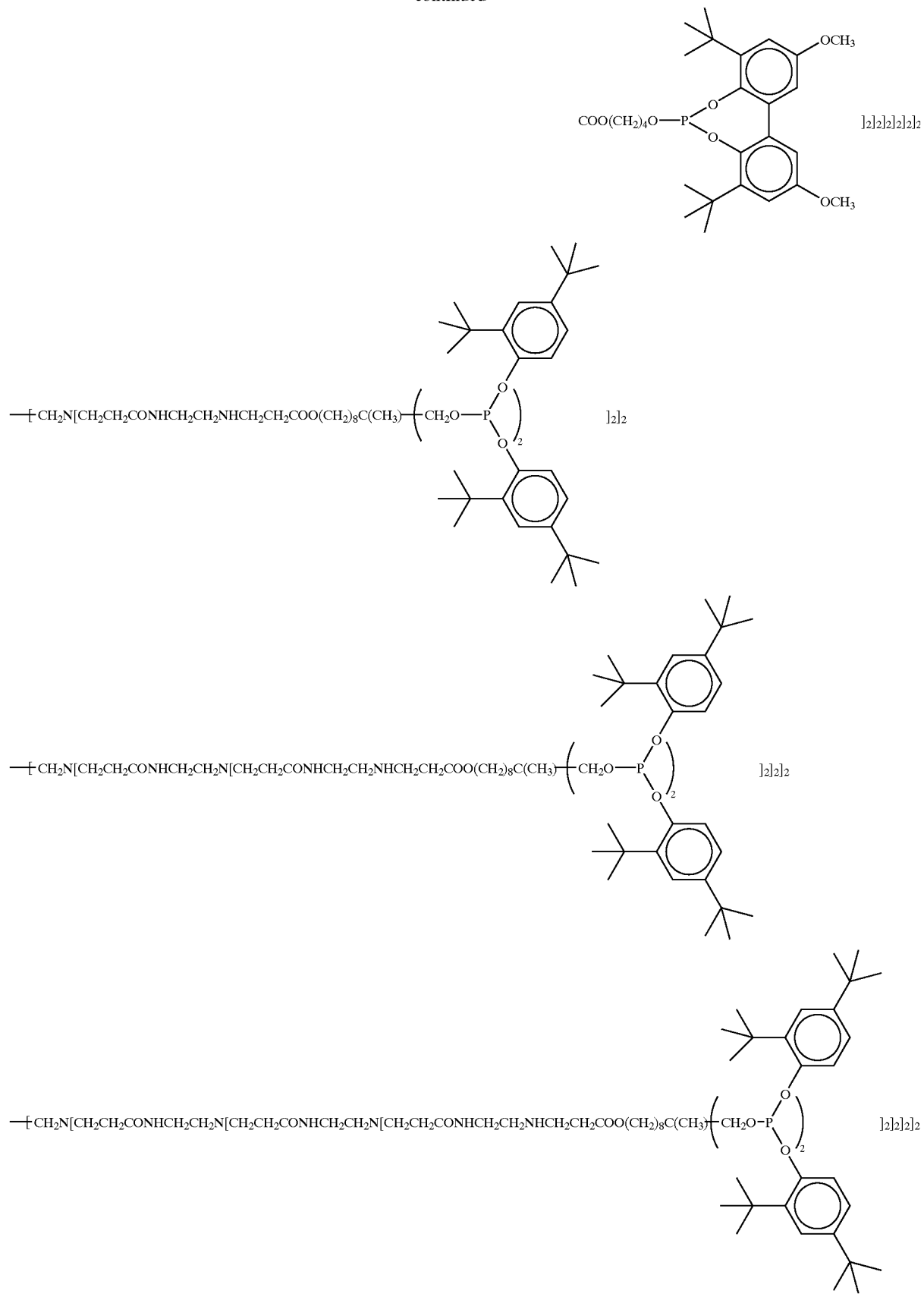

The molecular weights of the dendritic macromolecules of this invention should be greater than about 2,500, preferably from about 5,000 to 200,000, and more preferably from about 10,000 to 80,000. The dimensions of the dendritic macromolecules of this invention should include three-dimensional molecular diameters greater than about 20 Angstrom units, preferably from about 30 to 150 Angstrom units, and more preferably from about 40 to 90 Angstrom units. The dendritic macroligands need to be sufficiently soluble in the reaction solvent to provide a catalytically active amount for use in the processes of this invention. At least about 10 percent of dendrimer end groups should be functionalized with organophosphite-containing groups, preferably more than about 80 percent, more preferably from about 90 percent to 100 percent.

The metal-dendritic macroligand complex catalysts are preferably in homogeneous form. For instance, preformed rhodium hydrido-carbonyl-organophosphite ligand catalysts may be prepared and introduced into the reaction mixture of a particular process. More preferably, the metal-dendritic macroligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphite-containing dendritic macroligand for the in situ formation of the active catalyst.

As noted above, the dendritic macromolecules can be employed as the ligand of the metal-dendritic macroligand complex catalyst of the processes of this invention. In addition, it is to be understood that different types of dendritic macroligands, as well as, mixtures of two or more different dendritic macroligands or dendritic and non-dendritic macroligands may be employed in any given process, if desired.

The amount of metal-dendritic macroligand complex catalyst present in the reaction medium of a given process of this invention need only be that minimum amount necessary to provide the given metal concentration desired to be employed and which will furnish the basis for at least that catalytic amount of metal necessary to catalyze the particular process desired. In general, metal concentrations in the range of from about 1 part per million to about 10,000 parts per million, calculated as free metal, and dendritic macroligand to metal mole ratios in the catalyst solution ranging from about 1:1 or less to about 200:1 or greater, should be sufficient for most processes.

As noted above, in addition to the metal-dendritic macroligand complex catalysts, the processes of this invention and especially the hydroformylation process can be carried out in the presence of free terminal organophosphite groups, i.e., terminal organophosphite groups on the branches of the dendritic macromolecule that are not complexed with the metal. While the processes of this invention may be carried out in any excess amount of free terminal organophosphite groups desired, the employment of free terminal organophosphite groups may not be absolutely necessary. Accordingly, in general, the ratio of organophosphite groups to metal (P/M ratio) should be at least about 1, preferably about 2 to about 100, and more preferably about 4 to about 20. Such amounts of organophosphite groups and metal (e.g., rhodium) should be suitable for most purposes, particularly with regard to rhodium catalyzed hydroformylation.

The permissible reaction conditions employable in the processes of this invention are, of course, chosen depending on the particular syntheses desired. Such process conditions are well known in the art. All of the processes of this invention can be carried out in accordance with conventional procedures known in the art. Illustrative reaction conditions for conducting the processes of this invention are described, for example, in Kirk-Othmer, Encyclopedia of Chemical Technology, Fourth Edition, 1996, the pertinent portions of which are incorporated herein by reference. Depending on the particular process, operating temperatures may range from about −80° C. or less to about 500° C. or greater and operating pressures can range from about 1 psig or less to about 10,000 psig or greater.

The processes of this invention are conducted for a period of time sufficient to produce the desired products. The exact reaction time employed is dependent, in part, upon factors such as temperature, pressure, nature and proportion of starting materials, and the like. The reaction time will normally be within the range of from about one-half to about 200 hours or more, and preferably from less than about one to about 10 hours.

The processes of this invention are useful for preparing substituted and unsubstituted optically active and non-optically active compounds. Illustrative compounds prepared by the processes of this invention include, for example, substituted and unsubstituted alcohols or phenols; amines; amides; ethers or epoxides; esters; ketones; aldehydes; and nitriles. Illustrative of suitable optically active and non-optically active compounds which can be prepared by the processes of this invention (including starting material compounds as described hereinabove) include those permissible compounds which are described in Kirk-Othmer, Encyclopedia of Chemical Technology, Fourth Edition, 1996, the pertinent portions of which are incorporated herein by reference, and The Merck Index, An Encyclopedia of Chemicals, Drugs and Biologicals, Eleventh Edition, 1989, the pertinent portions of which are incorporated herein by reference.

In accordance with this invention, the products may be separated from the catalyst and other components of the crude reaction mixtures by conventional separation techniques. Separation of products from catalysts can be effected, for example, by membrane filtration, dialysis, precipitation or centrifugation. Preferably, membrane separation is used. Ultrafiltration or nanofiltration may be employed with commercially available membranes.

The processes of this invention can be conducted in a batch or continuous fashion, with recycle of unconsumed starting materials if required. The reaction can be conducted in a plurality of reaction zones, in series or in parallel or it may be conducted batchwise or continuously in an elongated tubular zone or series of such zones. For example, a back-mixed reactor may be employed in series with a multistaged reactor with the backmixed reactor being first. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more reaction steps and more than one reactive stages. The exact number of reaction steps and reactive stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

Metal leaching is a significant problem associated with regular polymeric catalysts. Such leaching is known in the art and described in greater detail, for example, in M. Beller et al., *J Mol. Catal.* A, 1995, 104, 17–85, and T. Jongsma et al., *Polymer*, 1992, 83, 161–165. The chemical nature of leaching with polymeric ligands presumably involves an equilibrium between the ligand-bound and "free" rhodium as follows:

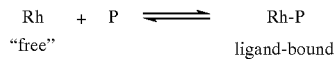

The "free" rhodium species have small dimensions and apparently pass through the membrane with the product. As a result of leaching, the rhodium recovery in a hydroformylation process with polymeric ligands suffers from rhodium loss. For example, at least 0.2% of rhodium has remained with the product after ultrafiltration separation using polymeric oxo ligands as disclosed in the article of S. B. Tupitsin and N. S. Imyanitov, *Neftekhimiya*, 1996, 36, 249–254.

It has been discovered that rhodium leaching virtually does not happen during the separation of the aldehyde product mixtures from the dendrimer-based catalyst. The level of rhodium in the product (permeates) was extremely low. The practical absence of metal leaching in case of dendrimeric ligands is an unexpected and propitious phenomenon and may be explained by several reasons. Surface phosphite groups of the dendrimeric ligands are located in close proximity due to the precise structure and may chelate rhodium species tightly enough to prevent rhodium from leaching. This capacity of dendrimeric ligands presumably shows up under reduced syngas pressure or in the absence of syngas similarly to that of indicator ligands disclosed in U.S. Pat. Nos. 5,741,943 and 5,741,945. Such strong rhodium coordination with phosphites does not occur in the case of regular polymeric ligands due to the haphazard location of phosphorus sites throughout the polymer structure.

Another reason for retaining rhodium with dendrimeric ligands may occur due to the functional groups such as amino, amide, ester, ether, thio, keto, and the like located throughout the dendrimer framework. This functionality can bind rhodium under syngas deficiency conditions during the separation and also prevent rhodium from leaching into the system.

Hydroformylation Processes

A preferred process useful in this invention is hydroformylation. The hydroformylation processing techniques of this invention may correspond to any known processing techniques. Preferred processes are those involving catalyst liquid recycle hydroformylation processes.

In general, such catalyst liquid recycle hydroformylation processes involve the production of aldehydes by reacting an olefinic unsaturated compound with carbon monoxide and hydrogen in the presence of a metal-dendritic macroligand complex catalyst in a liquid medium that also contains a solvent for the catalyst and dendritic macroligand. The recycle procedure generally involves withdrawing a portion of the liquid reaction medium containing the catalyst and aldehyde product from the hydroformylation reactor (i.e., reaction zone), either continuously or intermittently, and recovering the aldehyde product therefrom in accordance with the separation techniques of this invention.

In a preferred embodiment, the hydroformylation reaction mixtures employable herein includes any mixture derived from any corresponding hydroformylation process that contains at least some amount of four different main ingredients or components, i.e., the aldehyde product, a metal-dendritic macroligand complex catalyst and an organic solubilizing agent, e.g., polar or nonpolar solvent, for said catalyst, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid or solid aldehyde condensation byproducts, as well as other inert co-solvent, e.g., polar solvent, type materials or hydrocarbon additives, if employed. By the avoidance of vaporization as a separation means, generation of high boiling aldehyde condensation byproducts is minimized.

The substituted or unsubstituted olefin reactants that may be employed in the hydroformylation processes (and other suitable processes) of this invention include both optically active (prochiral and chiral) and non-optically active (achiral) olefinic unsaturated compounds containing from 2 to 40, preferably 2 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U. S. Pat. Nos. 4,518,809 and 4,528,403). Moreover, such olefin compounds may further contain one or more ethylenic unsaturated groups, and of course, mixtures of two or more different olefinic unsaturated compounds may be employed as the starting material if desired. For example, commercial alpha olefins containing four or more carbon atoms may contain minor amounts of corresponding internal olefins and/or their corresponding saturated hydrocarbon and that such commercial olefins need not necessarily be purified from same prior to being reacted. Illustrative mixtures of olefinic starting materials that can be employed in the hydroformylation reactions include, for example, mixed butenes, e.g., Raffinate I and II. Further such olefinic unsaturated compounds and the corresponding products derived therefrom may also contain one or more groups or substituents which do not unduly adversely affect the processes of this invention such as described, for example, in U. S. Pat. Nos. 3,527,809, 4,769,498 and the like.

Most preferably the subject invention is especially useful for the production of non-optically active aldehydes, by hydroformylating achiral alpha-olefins containing from 2 to 30, preferably 2 to 20, carbon atoms, and achiral internal olefins containing from 2 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, pentenoic acids and salts, e.g., salts of 3- and 4-pentenoic acids, alkyl alkenoates, e.g., methyl pentenoate, alkenyl alkanoates, alkenyl alkyl ethers, alkenols, e.g., pentenols, alkenals, e.g., pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Illustrative prochiral and chiral olefins useful in the asymmetric hydroformylation processes (and other asymmetric processes) that can be employed to produce enantiomeric product mixtures that may be encompassed by in this invention include those represented by the formula:

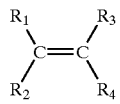

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation processes (and other asymmetric processes) of this invention include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360,938 and 5,491,266, the disclosures of which are incorporated herein by reference.

Illustrative of suitable substituted and unsubstituted olefinic starting materials include those permissible substituted and unsubstituted olefinic compounds described in Kirk-Othmer, Encyclopedia of Chemical Technology, Fourth Edition, 1996, the pertinent portions of which are incorporated herein by reference.

As noted, the hydroformylation processes of this invention involve the use of a metal-dendritic macroligand complex catalyst as described hereinabove. Of course mixtures of such catalysts can also be employed if desired. The amount of metal-dendritic macroligand complex catalyst present in the reaction medium of a given hydroformylation process encompassed by this invention need only be that minimum amount necessary to provide the given metal concentration desired to be employed and which will furnish the basis for at least the catalytic amount of metal necessary to catalyze the particular hydroformylation process involved such as disclosed, for example, in the above-mentioned patents. In general, metal, e.g., rhodium, concentrations in the range of from about 10 parts per million to about 1000 parts per million, calculated as free rhodium, in the hydroformylation reaction medium should be sufficient for most processes, while it is generally preferred to employ from about 10 to 500 parts per million of metal, e.g., rhodium, and more preferably from 25 to 400 parts per million of metal, e.g., rhodium.

In addition to the metal-dendritic macroligand complex catalysts, the hydroformylation processes of this invention can be carried out in the presence of free terminal organophosphite groups, i.e., terminal organophosphite groups on the branches of the dendritic macromolecule that are not complexed with the metal. While the hydroformylation processes of this invention may be carried out in any excess amount of free terminal organophosphite groups desired, the employment of free terminal organophosphite groups may not be absolutely necessary. Accordingly, in general, the ratio of organophosphite groups to metal (P/M ratio) should be at least about 1, preferably about 2 to about 100, and more preferably about 4 to about 20. Such amounts of organophosphite groups and metal (e.g., rhodium) should be suitable for most purposes, particularly with regard to rhodium catalyzed hydroformylation.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 2000 psia and more preferably less than about 1000 psia. The minimum total pressure is limited predominately by the amount of reactants necessary to obtain a desired rate of reaction. More specifically the carbon monoxide partial pressure of the hydroformylation process of this invention is preferable from about 1 to about 1000 psia, and more preferably from about 3 to about 800 psia, while the hydrogen partial pressure is preferably about 5 to about 500 psia and more preferably from about 10 to about 300 psia. In general $H_2$:CO molar ratio of gaseous hydrogen to carbon monoxide may range from about 1:10 to 100:1 or higher, the more preferred hydrogen to carbon monoxide molar ratio being from about 1:10 to about 10:1. Further, the hydroformylation process may be conducted at a reaction temperature from about −25° C. to about 200 ° C. In general hydroformylation reaction temperatures of about 50° C. to about 120° C. are preferred for all types of olefinic starting materials. Of course it is to be understood that when non-optically active aldehyde products are desired, achiral type olefin starting materials and dendritic macroligands are employed and when optically active aldehyde products are desired prochiral or chiral type olefin starting materials and dendritic macroligands are employed. Of course, it is to be also understood that the hydroformylation reaction conditions employed will be governed by the type of aldehyde product desired.

Accordingly illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, formylvaleric acids and salts, e.g., salts of 5-formylvaleric acid, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl- 1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl) propionaldehyde, S-2-(3-fluoro-4-phenyl) phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like.

Illustrative of suitable substituted and unsubstituted aldehyde products include those permissible substituted and unsubstituted aldehyde compounds described in Kirk-Othmer, Encyclopedia of Chemical Technology, Fourth Edition, 1996, the pertinent portions of which are incorporated herein by reference.

In accordance with this invention, the aldehyde product mixtures may be separated from the catalyst and other components of the crude reaction mixtures in which the aldehyde mixtures are produced by conventional separation as described above. Separation of products from catalysts can be effected, for example, by membrane filtration, dialysis, precipitation or centrifugation. Preferably, membrane separation is used. Ultrafiltration or nanofiltration may be employed with commercially available membranes. See, for example, U.S. Pat. No. 5,681,473 and T. C. Dickenson, *Filters and Filtration Handbook*, 4th Edition, Elsevier Advanced Technology, Oxford, UK, 1997, the disclosures of which are incorporated herein by reference.

It is generally preferred to carry out the hydroformylation processes of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a nonpolar solvent, the metal-dendritic macroligand complex catalyst and optionally a polar solvent; (b) maintaining reaction temperature and pressure conditions favorable to the hydroformylation of the olefinic starting material (s); (c) supplying make-up quantities of the olefinic starting material(s), carbon monoxide and hydrogen to the reaction medium as those reactants are used up; (d) separating the desired aldehyde hydroformylation product(s) from the reaction medium; and (e) recovering the desired aldehyde product(s).

At the conclusion of (or during) the process of this invention, the desired aldehydes may be recovered from the reaction mixtures used in the process of this invention. For instance, in a continuous liquid catalyst recycle process the portion of the liquid reaction mixture (containing aldehyde product, catalyst, etc.) removed from the reaction zone can be passed to a separation zone wherein the desired aldehyde product can be separated from the liquid reaction mixture, and further purified if desired. The remaining catalyst containing liquid reaction mixture may then be recycled back to the reaction zone as may if desired any other materials, e.g., unreacted olefin, together with any hydrogen and carbon monoxide dissolved in the liquid reaction after separation thereof from the aldehyde product.

In addition to their usefulness as ligands in metal-ligand complex catalyzed processes, the dendritic macromolecules of this invention may be useful in coatings, plastic additives, cosmetics, adhesives, lubricants, agricultural chemicals, pharmaceutical or medicinal uses, and the like.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate this invention.

EXAMPLE 1

4-Hydroxybutyl acrylate (8.7 grams; 60 millimoles) in 100 milliliters of toluene was mixed with pyridine (6.8 grams; 85 millimoles) and added dropwise to (3,3'-di-tert-butyl-5,5'-dimethoxy-1,1'-biphenyl-2,2'-diyl) phosphorochloridite (34 grams; 80 millimoles) in 80 milliliters of toluene under stirring. White compound precipitated during the course of addition. The reaction progress was followed by thin layer chromatography (hexane-ethyl acetate 10:1).

The mixture was filtered, toluene was evaporated, and the residue was flash chromatographed on silica gel using hexane-ethyl acetate 10:1. The solvent was evaporated to give 26.0 grams (82%) of a solid having the formula below (ligand precursor I). $^{31}P\{^{1}H\}$ NMR ($\delta$, $C_6D_6$, ppm): 135.6, singlet. $^{1}H$ NMR ($\delta$, $C_6D_6$, ppm): 1.508 (s, 18 H, ortho t-Bu), 1.2–1.5 (m, 4H, $C_2H_4$), 3.337 (s, 6H, two $CH_3O$), 3.76–3.92 (m, 4 H, two $CH_2O$), 5.2–6.3 (m, ABX system, $CH_2$=CH), 6.716 and 7.145 (two d, J=3.0 Hz, 4 H, arom).

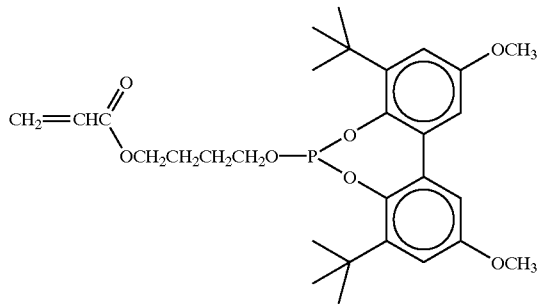

EXAMPLE 2

In a manner similar to Example 1, a reaction between 4-hydroxybutyl acrylate and (3,3',5,5'-tetra-tert-butyl-1,1'-biphenyl-2,2'-diyl) phosphorochloridite resulted in a viscous liquid solidified under vacuum and having the formula below (ligand precursor II). $^{31}P\{^{1}H\}$ NMR ($\delta$, $C_6D_6$, ppm): 136.8, singlet. $^{1}H$ NMR ($\delta$, $C_6D_6$, ppm): 1.493 (s,18 H, para t-Bu), 1.641 (s, 18 H, ortho t-Bu), 1.3–1.8 (m, 4H, $C_2H_4$), 3.92–3.98 (m, 2 H, $CH_2O$), 4.248 (t, 2 H, J=6 Hz, $COOCH_2$), 5.8–6.6 (m, ABX system, $CH_2$=CH), 7.333 and 7.581 (two d, J=2.4 Hz, 4 H, arom).

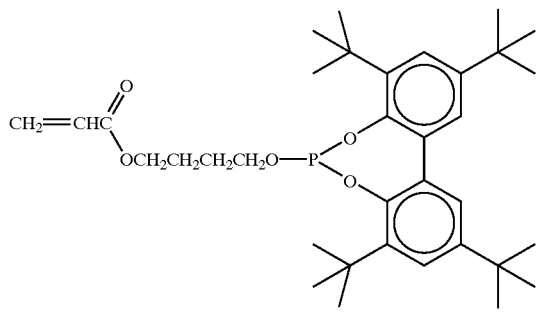

EXAMPLE 3

Ligand precursor I (3.8 grams; 7.2 millimoles) and Starburst™ (PAMAM) Dendrimer, Generation 0 (available from Aldrich) (0.786 grams; 6.08 millimoles) were refluxed in 300 milliliters of iso-propanol for 16 hours. Rimini's test of the reaction mixture with disodium pentacyanonitrosoferrate (III) (nitroprusside) showed absence of primary amino groups of the starting Starburst™ (PAMAM) Dendrimer. Iso-propanol was removed in vacuum, then 4 milliliters of iso-propanol was added to dissolve the residue followed by addition of 200 milliliters of hexane upon reflux. The mixture was cooled to 0° C., the solid was filtered off and dried in vacuum for 1 hour to give 2.9 grams (72%) of the product (referred to as G0 Dendrophite) with a melting point of 65–68° C. having the formula represented below. $^{31}P\{^{1}H\}$ NMR ($\delta$, dmso-$d_6$, ppm): 137.75, singlet. $^{13}C\{^{1}H\}$ NMR ($\delta$, dmso-$d_6$, ppm): 24.54, 27.01, 30.52, 30.49, 34.89, 44.54, 48.39, 55.30, 63.15, 64.20 (dendrimer+end group aliphatic chain); 112.94, 114.15, 132.93 (J=3.4 Hz), 141.18 (J=5.5 Hz), 141.43, 155.30 (aromatic); 171.26, 171.93 (amide and ester groups). Anal. Calcd. for $C_{138}H_{204}N_{10}O_{32}P_4$ (MW=2,639.08): C, 62.81; H, 7.79; N, 5.31; P, 4.69. Found: C, 62.37; H, 7.82; N, 5.15; P, 4.76.

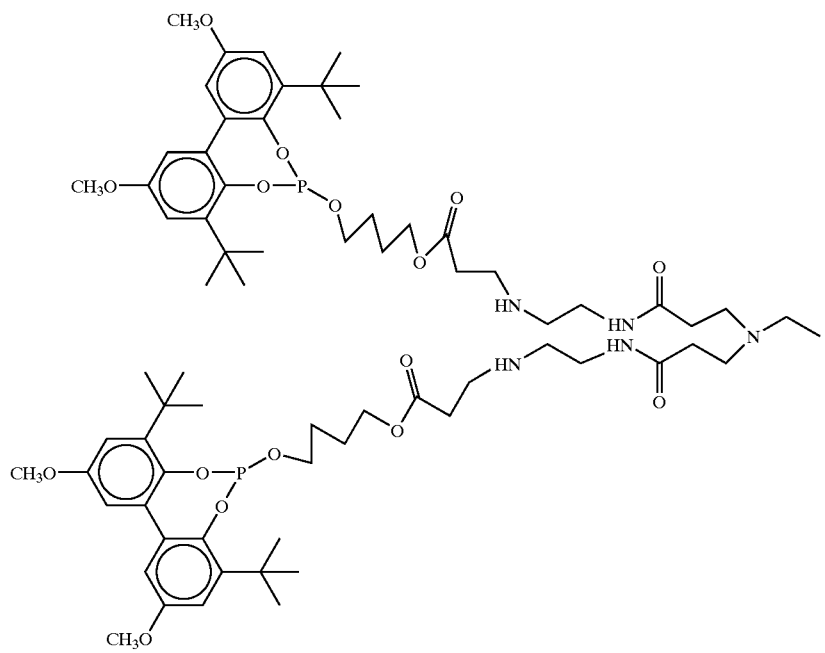

-continued

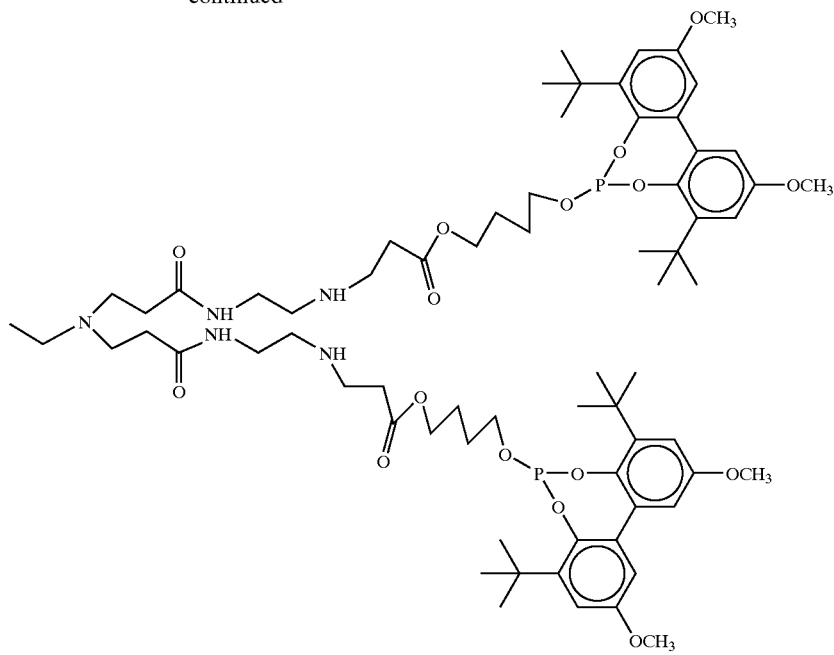

EXAMPLE 4

In a manner similar to Example 3, a reaction between ligand precursor I and Starburst ™ (PAMAM) Dendrimer, Generation 1 (available from Aldrich), resulted in the product (yield 79%) having the formula depicted below (referred to as G 1 Dendrophite). $^{31}P\{^1H\}$ NMR (δ, dmso-$d_6$, ppm): 137.74, singlet. $^{13}C\{^1H\}$ NMR (δ, dmso-$d_6$, ppm): 24.53, 25.47, 26.96, 26.99, 30.48, 30.49, 34.88, 44.54, 48.37, 55.29, 63.15, 64.22 (dendrimer+end group aliphatic chain); 112.93, 114.14, 132.93 (J=3.3 Hz), 141.17 (J=5.6 Hz), 141.42, 155.30 (aromatic); 171.27, 171.92 (amide and ester groups). Anal. Calcd. for $C_{294}H_{440}N_{26}O_{68}P_8$(MW=5,674.66): C, 62.23; H, 7.82; N, 6.42; P, 4.37. Found: C, 61.36; H, 7.76; N, 6.17; P, 4.56.

EXAMPLE 5

In a manner similar to Example 3, a reaction between ligand precursor I and Starburst ™ (PAMAM) Dendrimer, Generation 2 (available from Aldrich), resulted in the product (yield 72%) having the formula depicted below (referred to as G2 Dendrophite). $^{31}P\{^1H\}$ NMR (δ, dmso-$d_6$, ppm): 137.73, singlet. $^{13}C\{^1H\}$ NMR (δ, dmso-$d_6$, ppm): 24.53, 25.47, 26.96, 26.99, 30.48, 30.50, 30.67, 33.22, 34.45, 34.87, 44.52, 48.36, 49.59, 52.19, 55.27, 63.15, 64.19, 64.22 (dendrimer+end group aliphatic chain); 112.92, 114.13, 132.93 (J=3.4 Hz), 141.18 (J=5.5 Hz), 141.42, 155.30 (aromatic); 171.14, 171.29, 171.89 (amide and ester groups). Anal. Calcd. for $C_{606}H_{912}N_{58}O_{140}P_{16}$(MW=11,745.79): C, 61.97; H, 7.83; N, 6.92; P, 4.22. Found: C, 60.54; H, 7.70; N, 6.89; P, 3.51.

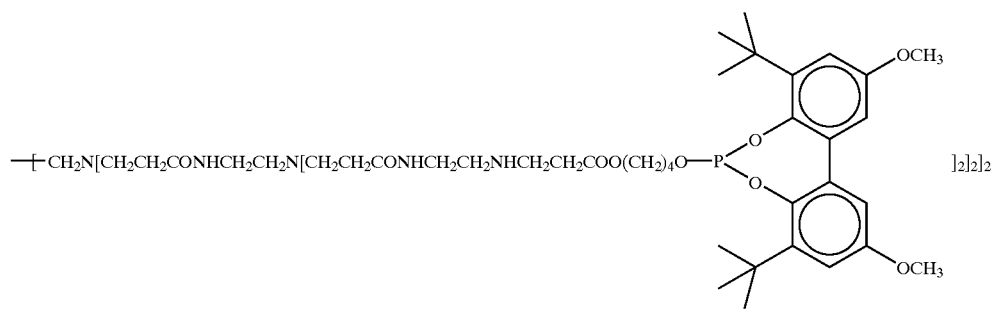

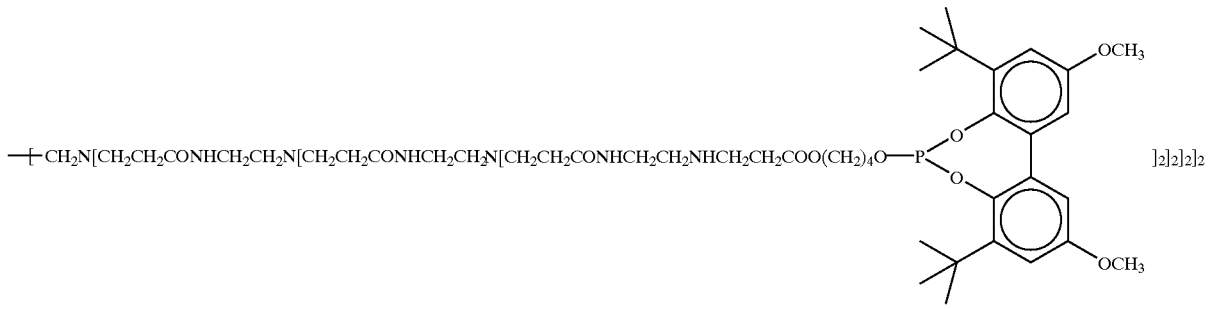

EXAMPLE 6

In a manner similar to Example 3, a reaction between ligand precursor I and Starburst ™ (PAMAM) Dendrimer, Generation 3 (available from Aldrich), resulted in the product (yield 70%) having the formula depicted below (referred to as G3 Dendrophite). $^{31}P\{^{1}H\}$ NMR (δ, dmso-d$_6$, ppm): 137.66, singlet. $^{13}C\{^{1}H\}$ NMR (δ, dmso-d$_6$, ppm): 24.53, 25.47, 26.97, 26.99, 30.46, 30.50, 30.49, 33.24, 34.45, 34.85, 44.52, 48.36, 49.59, 52.21, 52.23, 55.25, 63.13, 64.16, 64.18, 64.21 (dendrimer+end group aliphatic chain); 112.89, 114.11, 132.93 (J=3.4 Hz), 141.18 (J=5.3 Hz), 141.41, 155.28 (aromatic); 171.14, 171.29, 171.88, 171.91 (amide and ester groups). Anal. Calcd. for $C_{1230}H_{1856}N_{122}O_{284}P_{32}$ (MW=23,888.08): C, 61.84; H, 7.83; N, 7.15; P, 4.15. Found: C, 60.98; H, 7.95; N, 7.06; P, 4.27.

EXAMPLE 7

In a manner similar to Example 3, a reaction between ligand precursor I and Starburst ™ (PAMAM) Dendrimer, Generation 4 (available from Aldrich), resulted in the product (yield 75%) having the formula depicted below (referred to as G4 Dendrophite). $^{31}P\{^{1}H\}$ NMR (δ, dmso-d$_6$, ppm): 137.65, singlet. $^{13}C\{^{1}H\}$ NMR (δ, dmso-d$_6$, ppm): 24.52, 25.48, 26.94, 26.99, 30.46, 30.48, 33.23, 33.26, 34.46, 34.84, 44.52, 44.54, 48.36, 49.57, 49.61, 49.63, 55.24, 62.00, 63.12, 64.19 (dendrimer+end group aliphatic chain); 112.88, 114.11, 132.91 (J=3.3 Hz), 141.18 (J=5.5 Hz), 141.39, 155.27 (aromatic); 171.15, 171.17, 171.28, 171.89 (amide and ester groups). Anal. Calcd. for $C_{2478}H_{3742}N_{250}O_{572}P_{64}$ (MW=48,172.65): C, 61.84; H, 7.83; N, 7.15; P, 4.15. Found: C, 60.98; H, 7.95; N, 7.06; P, 4.27.

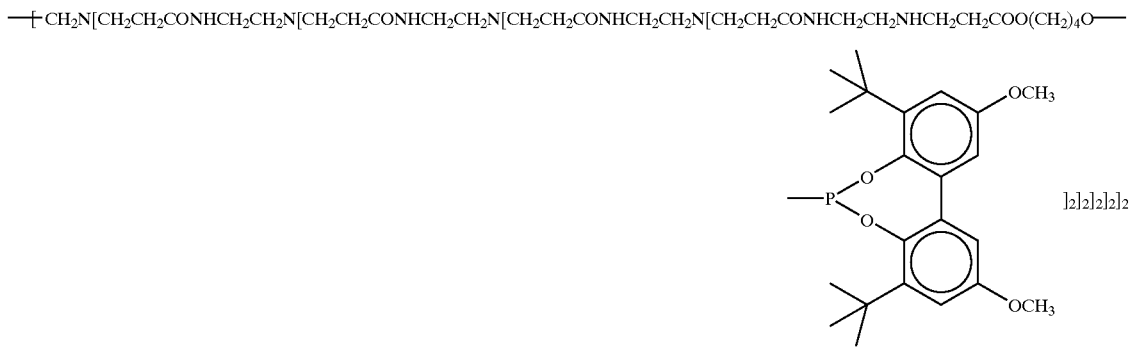

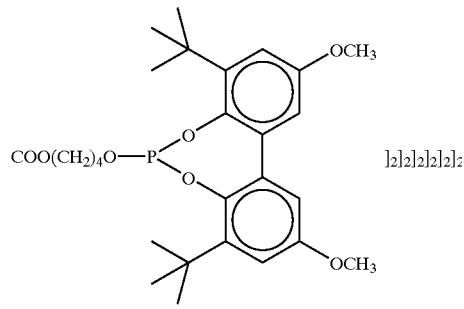

EXAMPLES 8–12

A catalyst solution was prepared consisting of 0.0101 grams (0.039 millimoles) of rhodium dicarbonyl acetylacetonate, 0.2362 grams (0.0048 millimoles) of G4 Dendrophite prepared in Example 7 (1:8 Rh to P ratio) and 20 grams of Texanol® solvent. This solution (15 grams) was charged to a 100 milliliter stainless steel reactor and stirred for 1 hour at 70° C. under 50 psi $CO/H_2$ 1:1. Then the reactor was pressurized to 100 psi with $C_3H_6/CO/H_2$ 1:1:1. The rate of the reaction was determined by timing the drop in pressure as the gas mixture was consumed. The reaction was stopped after the consumption of 70–80 psi of the feedstock gas. A portion of the reaction mixture was analyzed by gas chromatography. Similar reactions were conducted using G0 Dendrophite (prepared in Example 3), G1 Dendrophite (prepared in Example 4), G2 Dendrophite (prepared in Example 5) and G3 Dendrophite (prepared in Example 6). The table below summarizes reaction rates and normal/branched ratios for reactions conducted using G0–G4 Dendrophites.

TABLE

| Ligand | MW | Rate, g-mol/l/h | N/I ratio |
| --- | --- | --- | --- |
| G0 Dendrophite | 2,639 | 3.2 | 1.32 |
| G1 Dendrophite | 5,675 | 2.9 | 1.38 |
| G2 Dendrophite | 11,746 | 2.0 | 1.41 |
| G3 Dendrophite | 23,888 | 1.9 | 1.38 |
| G4 Dendrophite | 48,173 | 1.8 | 1.40 |

(Conditions: Rh 200 ppm; Rh:P 1:8; 70° C.; 100 psi $C_3H_6$:CO:$H_2$; solvent—Texanol®)

EXAMPLES 13–27

The dump hydroformylation mixtures in Texanol® solvent from Examples 8–12 were passed through reverse osmosis (nanofiltration) membranes MPF-50 (available from Membrane Products Kiryat Weizmann Ltd., Israel), crosslinked GKSS with a 10 □m active layer thickness and GKSS with a 1 μm active layer thickness (both available from GKSS, Forschungszentrum Geesthacht GmbH, Germany). The experimental setup is described in Example 1 of U.S. Pat. No. 5,681,473, supra. The feed was pumped into the unit at a flow rate of 100 milliliters per minute and at pressures of 300 psig for MPF-50 and GKSS (1 μm) and 150 psig for GKSS (10 μm). All tests were conducted at room temperature under nitrogen. All three membranes proved resistant to Texanol® solvent and the aldehydes in preliminary tests. Rhodium rejection was determined according to the formula:

Rejection=[1 −Permeate Conc./0.5(Feed Conc.+Raffinate Conc.)]× 100%

The total volume of permeate collected from each membrane area over a specified period of time was used to calculate the permeate flux in gallon/foot$^2$/day (GFD). The table below summarizes Rh rejections and permeation rates for the reverse osmosis membranes using G0–G4 Dendrophites. Amounts of macroligands were undetectable in the permeate solutions.

TABLE

| Dendrimer generation | MPF-50 | | GKSS (1 μm) | | GKSS (10 μm) | |
| --- | --- | --- | --- | --- | --- | --- |
| | % Rh rejection | Flux rate (GFD) | % Rh rejection | Flux rate (GFD) | % Rh rejection | Flux rate (GFD) |
| G0 | 99.59 | 0.15 | 99.60 | 0.70 | 99.84 | 0.20 |
| G1 | 99.74 | 0.34 | 99.86 | 0.52 | 99.86 | 0.30 |
| G2 | 99.88 | 0.11 | 99.95 | 0.14 | 99.96 | 0.18 |
| G3 | 99.92 | 0.10 | 99.94 | 0.24 | 99.96 | 0.24 |
| G4 | 99.89 | 0.063 | 99.93 | 0.063 | 99.94 | 0.067 |

Comparative Example 1

The procedure of Examples 13–27 was repeated using Ligand A depicted below in place of the G0–G4 Dendrophites. Rh rejection of the MPF-50 membrane was 65% and the permeate flux was about 0.3–0.5 GFD. Rh rejection of the GKSS (10 μm) membrane was 88% and the permeate flux was about 0. 15–0.2 GFD.

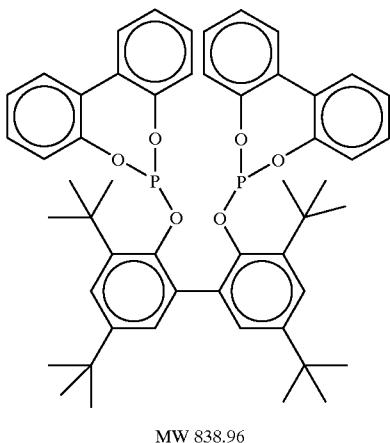

Ligand A

MW 838.96

EXAMPLES 28–32

The procedure described in Examples 13–27 was repeated with the modification of using a 50 Angstrom unit ultrafiltration membrane (commercially available from US Filter/Membralox, Warrendale, Pennsylvania) in place of the reverse osmosis membranes and toluene in place of Texanol® as a solvent. The table below summarizes Rh rejections and permeation rates for the ultrafiltration membrane using different generations of Dendrophites. Amounts of macroligands were undetectable in the permeate solutions.

TABLE

| Dendrimer generation | Cycle | % Rh rejection | Flux rate (GFD) |
|---|---|---|---|
| G2 | 1st | 99.994 | 2.0 |
| G3 | 1st | 99.997 | 1.9 |
| G4 | 1st | 99.9975 | 1.3 |
| G4 | 2nd | 99.9974 | 2.2 |
| G4 | 3rd | 99.994 | 2.1 |

Comparative Example 2

The procedure of Examples 28–32 was repeated using Ligand B depicted below in place of the G2–G4 Dendrophites. Rh rejection of the ultrafiltration membrane was only 83–86% and the permeate flux was about 4.2 GFD.

Ligand B

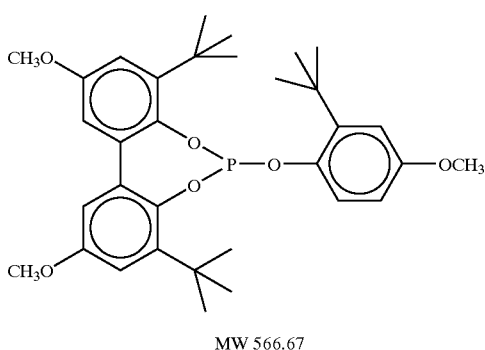

MW 566.67

EXAMPLE 33

The procedure described in Examples 8–12 was repeated with catalysts based on G3 Dendrophite with the modification of using toluene in place of Texanol® solvent, and the hydroformylation rates for these initial solutions were measured. The reaction mixtures were passed through the 50 Å ultrafiltration membrane and the rates were measured again for the raffinates (catalyst solutions retained by the membrane). The rate differences for the initial solutions and the raffinates were only 2% for the G2 Dendrophite and 3% for the G3 Dendrophite. Rhodium concentrations in the initial solutions and raffinates were adjusted for comparison accordingly. $^{31}$P NMR analysis of the raffinates showed macroligand integrity for G2, G3 and G4 Dendrophites.

Although the invention has been illustrated by the preceding example, it is not to be construed as being limited thereby; but rather, the invention encompasses the generic area as hereinbefore disclosed. Various modifications and embodiments can be made without departing from the spirit and scope thereof.

What is claimed is:

1. A metal-dendritic macroligand complex catalyst comprising a Group 8, 9 or 10 metal complexed with a dendritic macroligand represented by the formula:

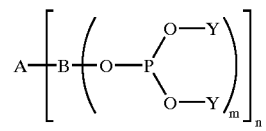

wherein A represents a q-valent dendritic macromolecule radical, each B is the same or different and represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, n is a value of from 1 to about 1000, q equals n, and r equals m+1.

2. A process for producing one or more products comprising reacting one or more reactants in the presence of a metal-dendritic macroligand complex catalyst to produce said one or more products, in which said metal-dendritic macroligand complex catalyst comprises a Group 8, 9 or 10 metal complexed with a dendritic macroligand represented by the formula:

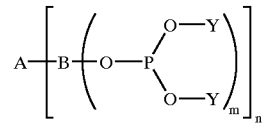

wherein A represents a q-valent dendritic macromolecule radical, each B is the same or different and represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, n is a value of from 1 to about 1000, q equals n, and r equals m+1.-

3. A process for producing one or more products comprising (i) reacting one or more reactants in the presence of a metal-dendritic macroligand complex catalyst to produce said one or more products, and (ii) separating said metal-dendritic macroligand complex catalyst from said one or more products, wherein said metal-dendritic macroligand complex catalyst comprises a Group 8, 9 or 10 metal complexed with a dendritic macroligand represented by the formula:

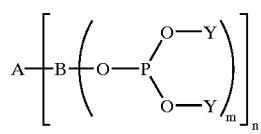

wherein A represents a q-valent dendritic macromolecule radical, each B is the same or different and represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, n is a value of from 1 to about 1000, q equals n, and r equals m+4.

4. The process of claim 2 which comprises a hydroformylation, hydroacylation (intramolecular and intermolecular), hydrocyanation, hydroamidation, hydroesterification, amination (hydro-amino-addition), alcoholysis (hydro-alkoxy-addition), hydrocarbonylation, hydroxycarbonylation, carbonylation, isomerization or transfer hydrogenation process.

5. The process of claim 2 wherein said metal-dendritic macroligand complex catalyst comprises rhodium complexed with a dendritic macroligand represented by the formula selected from:

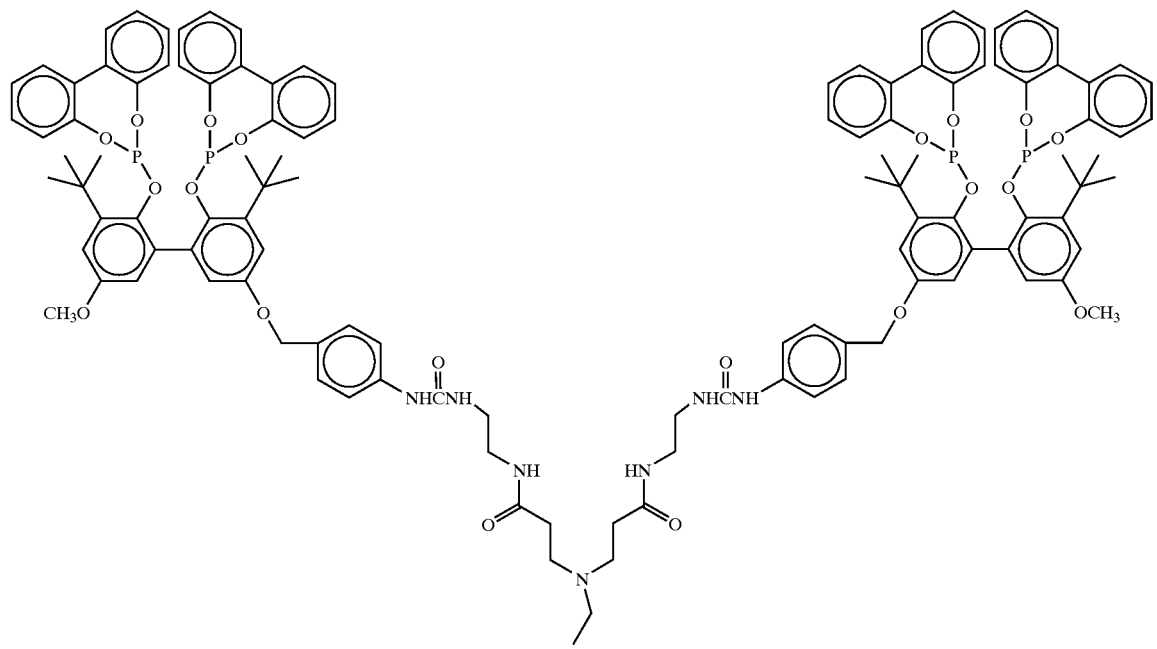

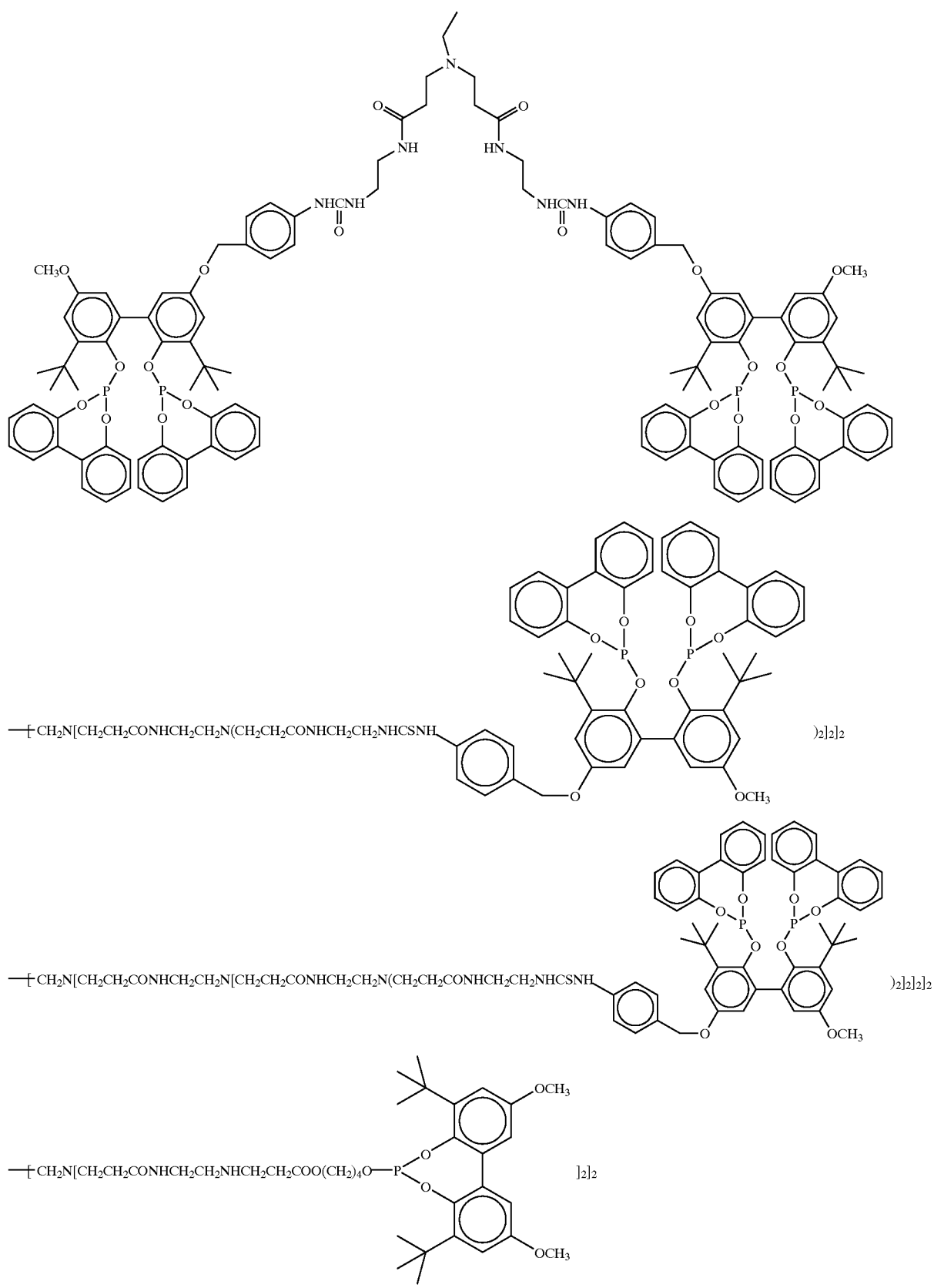

-continued
—[CH₂N[CH₂CH₂CONHCH₂CH₂N[CH₂CH₂CONHCH₂CH₂NHCH₂CH₂COO(CH₂)₄O—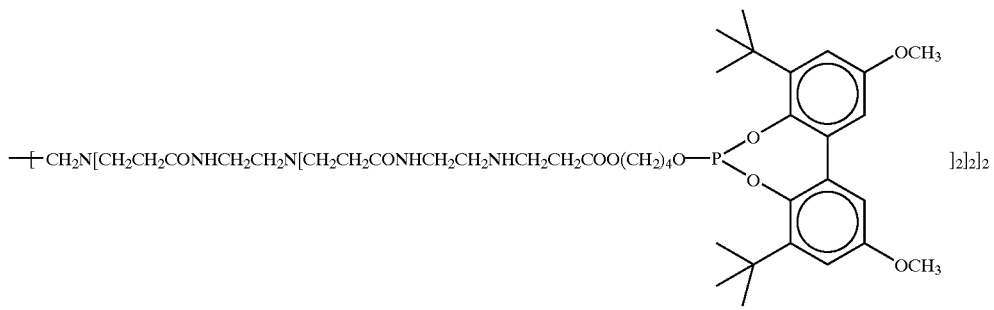]₂]₂]₂
—[CH₂N[CH₂CH₂CONHCH₂CH₂N[CH₂CH₂CONHCH₂CH₂N[CH₂CH₂CONHCH₂CH₂NHCH₂CH₂COO(CH₂)₄O—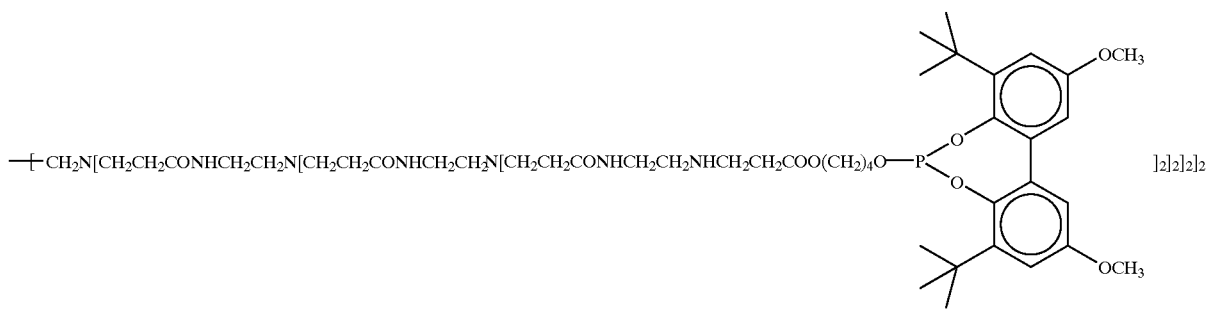]₂]₂]₂]₂
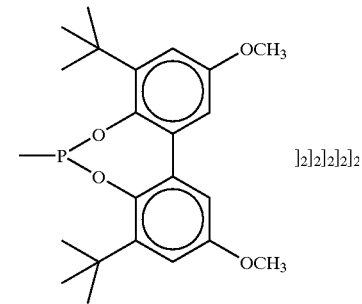
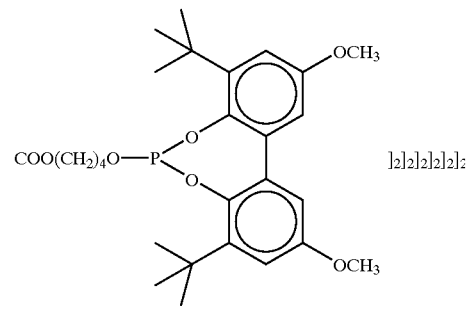

-continued

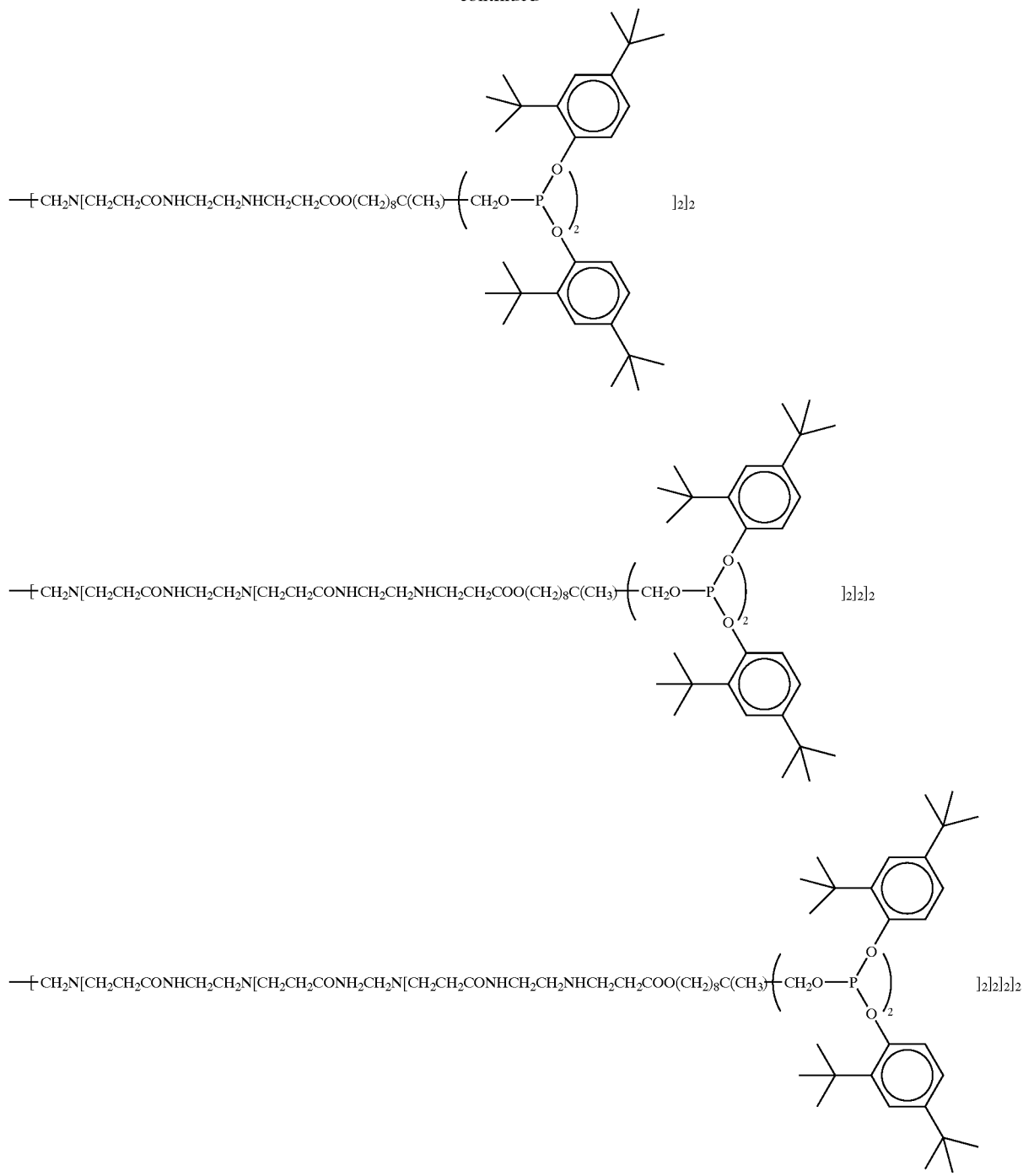

6. The process of claim 3 in which the separating step is effected by membrane filtration, dialysis, precipitation or centrifugation.

7. A functional organophosphite of the formula:

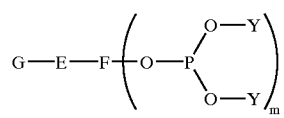

wherein G represents a functional organic or inorganic group which is capable of reacting with an end group of a dendrimer, E represents a substituted or unsubstituted divalent organic or inorganic radical, F represents a substituted or unsubstituted r-valent organic or inorganic radical, each Y is the same or different and represents a substituted or unsubstituted monovalent hydrocarbon radical containing from 6 to 40 carbon atoms or each adjacent Y may be bridged together to form a substituted or unsubstituted cyclic hydrocarbon radical, m is a value of from 1 to about 3, and r equals m+1.

* * * * *